(12) United States Patent
Rothblum

(10) Patent No.: US 9,675,662 B2
(45) Date of Patent: Jun. 13, 2017

(54) COMPOSITIONS FOR INHIBITION OF RNA POLYMERASE I AND METHODS OF PRODUCTION AND USE THEREOF

(75) Inventor: Lawrence Rothblum, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 28 days.

(21) Appl. No.: 13/309,651

(22) Filed: Dec. 2, 2011

(65) Prior Publication Data

US 2013/0143318 A1 Jun. 6, 2013

(51) Int. Cl.
| | | |
|---|---|---|
| *C07H 21/04* | (2006.01) | |
| *C07K 1/00* | (2006.01) | |
| *C12N 15/63* | (2006.01) | |
| *A61K 38/17* | (2006.01) | |
| *C12N 9/12* | (2006.01) | |
| *A01K 67/00* | (2006.01) | |

(52) U.S. Cl.
CPC ........ *A61K 38/1709* (2013.01); *C12N 9/1247* (2013.01); *C07K 2319/10* (2013.01)

(58) Field of Classification Search
CPC .............. A61K 38/1709; C12N 9/1247; C07K 2319/10
USPC .......................... 536/23.4; 530/361; 435/455
See application file for complete search history.

(56) References Cited

U.S. PATENT DOCUMENTS

| 2002/0090706 A1* | 7/2002 | Reeder et al. ................ 435/199 |
| 2004/0082029 A1* | 4/2004 | Lal et al. ..................... 435/69.1 |
| 2012/0020954 A1* | 1/2012 | Achiron et al. ........... 424/130.1 |

OTHER PUBLICATIONS

Gerhold et al. Its the genes! EST access to human genome content. BioEssays 18:973-981, 1996.*
Atwood, T.K. The Babel of Bioinformatics. Science 290:471-473, 2000.*
Peyroche et al. The recruitment of RNA polymerase I on rDNA is mediated by the interaction of the A43 subunit with Rrn3. EMBO J. 19:5473-5482, 2000.*
Cavanaugh et al. Rrn3 phosphorylation is a regulatory checkpoint for ribosome biogenesis. J. Biol. Chem. 277:27423-27432, 20002.*
Meade, Bryan R., et al.; "Exogenous siRNA delivery using peptide transduction domain/cell penetrating peptides"; Elesevier, Science Direct; (2007) vol. 59; pp. 134-140; last modified Mar. 2007.
Morris, May C., et al.; "Cell-penetrating peptides: from molecular mechanisms to therapeutics" (2008); Biol. Cell, vol. 100; pp. 201-217; (Printed in Great Britain) doi:10.1042/BC20070116.
Gros Edwige, et al.; "A non-covalent peptide-based strategy for protein and peptide nucleic acid transduction" (2006); Biochimica et Biophysica Acta; vol. 1758; pp. 284-393; last modified Feb. 2006.
Heitz, Frederic, et al.; "Themed Section Vector Design and Drug Delivery, Review, Twenty years of cell-penetrating peptides: from molecular mecanisms to therapeutics", British Journal of Pharmacology (2009); vol. 157; pp. 195-206.

* cited by examiner

*Primary Examiner* — Quang Nguyen
(74) *Attorney, Agent, or Firm* — Dunlap Codding, P.C.

(57) ABSTRACT

Compositions for inhibition of RNA Polymerase I include peptides of Rpa43. Methods of production and use thereof are also disclosed.

19 Claims, 12 Drawing Sheets

FIGURE 1

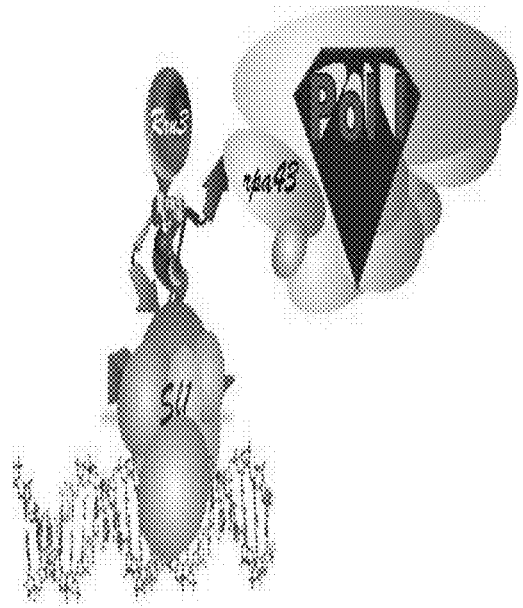

FIGURE 2

```
SEQ ID NO:
   177  --                   KKV SSSHIGCLVHGCFNASIPK
   178  --H. sapiens   LMGIVNKV SSSHIGCLVHGCFNASIPK PEQ
   179  --M. musculus  LMGTVNKV SSSHIGCLVHGCFNASIPK PEQ
   180  --B. taurus        GTVNKV SSSHIGCLVHGCFNASIPK
   181  --E. caballus      GTVNKV SSSHIGCLVHGCFNASIPK
   182  --X. laevis        GIVNKV APTHIGCLVHGCFNASIPK
   183  --D. rerio         GVINKM GASHVGCLVHGCFNASVMK PNAL
   184  --S. salar         TVNKL GVSHVGCLVHGCFNASVPK PAHVT
   185  --D. discoideum    VVKRV STTHISLLVFGTISASIPK SNIP
   186  --S. pombe         GKINLV SPSHIGLLILGIFNASIPR KSIPK DWIFIEPDTT
   187  --S. cerev.      L GYIFIQ SASHIGLLIHDAFNASIKK NNIPV DWIFVH
   188  --Consensus        G n v s SHIGcLVHGcFNASIPK
                                  t v l   l   i   v
```

Effects of TAT-22mer on the Growth of A431 Cells After 72 Hr

MTT Assay of STBY Peptide in NIH 3T3 cells 48 hours read 18 min after extraction 7-22-2011

WI38 cells take up TAT-22mer

Effect of TAT-22mer on WI38 Cells After 48 Hr Treatment (MTT Assay)

Effects of TAT-22mer on the Growth of U937 Cells After 24 Hr

Effects of TAT-22mer on the Growth of N1S1 Hepatoma Cells: (Fresh Peptide Added After 24 Hr)

Effects of TAT-22mer on the Growth of N1S1 Hepatoma Cells: (Fresh Peptide Added After 24 Hr)

Effect of TAT-22mer on P1798 Lymphosarcoma Cells

COMPOSITIONS FOR INHIBITION OF RNA POLYMERASE I AND METHODS OF PRODUCTION AND USE THEREOF

STATEMENT REGARDING FEDERALLY FUNDED RESEARCH OR DEVELOPMENT

This invention was made with government support under Contract Numbers GM069841 and HL077814 awarded by the National Institutes of Health. The government has certain rights in the invention.

CROSS REFERENCE TO RELATED APPLICATIONS

Not Applicable.

BACKGROUND

1. Field of the Invention

The presently disclosed and claimed inventive concept(s) is related in general to compositions for inhibition of ribosomal RNA synthesis, and methods of producing and using same.

2. Description of the Background

In 1934 W. C. MacCarthy published an article describing the irregular shapes of the nucleoli of cancer cells. This manuscript was the first to formally demonstrate that the nucleolus, the site of ribosomal RNA synthesis, was unusual in cancer cells. Subsequent studies have demonstrated highly elevated rates of rRNA synthesis in tumors and elevated rates in hypertrophic tissues. Hence, there has been a long-term goal to discover a method to specifically inhibit rDNA transcription in tumor cells.

Deregulated ribosomal RNA synthesis is associated with cancer cell proliferation. RNA polymerase I (Pol I), the multiprotein complex that synthesizes rRNA, is activated in most cancers. Thus, it is possible that selective inhibitors of Pol I and the transcription process may offer a general therapeutic strategy to inhibit cancer cell proliferation. Currently there are only two mechanisms that target transcription by RNA polymerase I in cancer cells. The first drug is actinomycin D, which has broad effects on cellular physiology. The second drug is CX-5461; this small molecule inhibitor of rDNA transcription is believed to act by blocking rDNA transcription initiation relative to its effects on transcription by RNA polymerase II, DNA replication and protein synthesis. However, its precise mechanism of action is not defined. Interestingly, CX-5461 does not induce apoptosis, which some have claimed to be the outcome of inhibiting rDNA transcription.

There exists a need in the art for new and improved compositions for inhibition of RNA Pol I, as well as methods of producing and using same. The presently disclosed and claimed inventive concept(s) is directed to said compositions and methods, which overcome the disadvantages and defects of the prior art.

BRIEF DESCRIPTION OF THE DRAWINGS

FIG. 1 illustrates that Rrn3 functions to recruit RNA polymerase I to the complex formed on the rDNA promoter as illustrated by SL1 bound to the rDNA promoter.

FIG. 2 depicts an alignment of the sequences of the conserved domain as found in Rpa43 in various eukaryotes.

DETAILED DESCRIPTION OF THE INVENTIVE CONCEPT(S)

Figure 3:
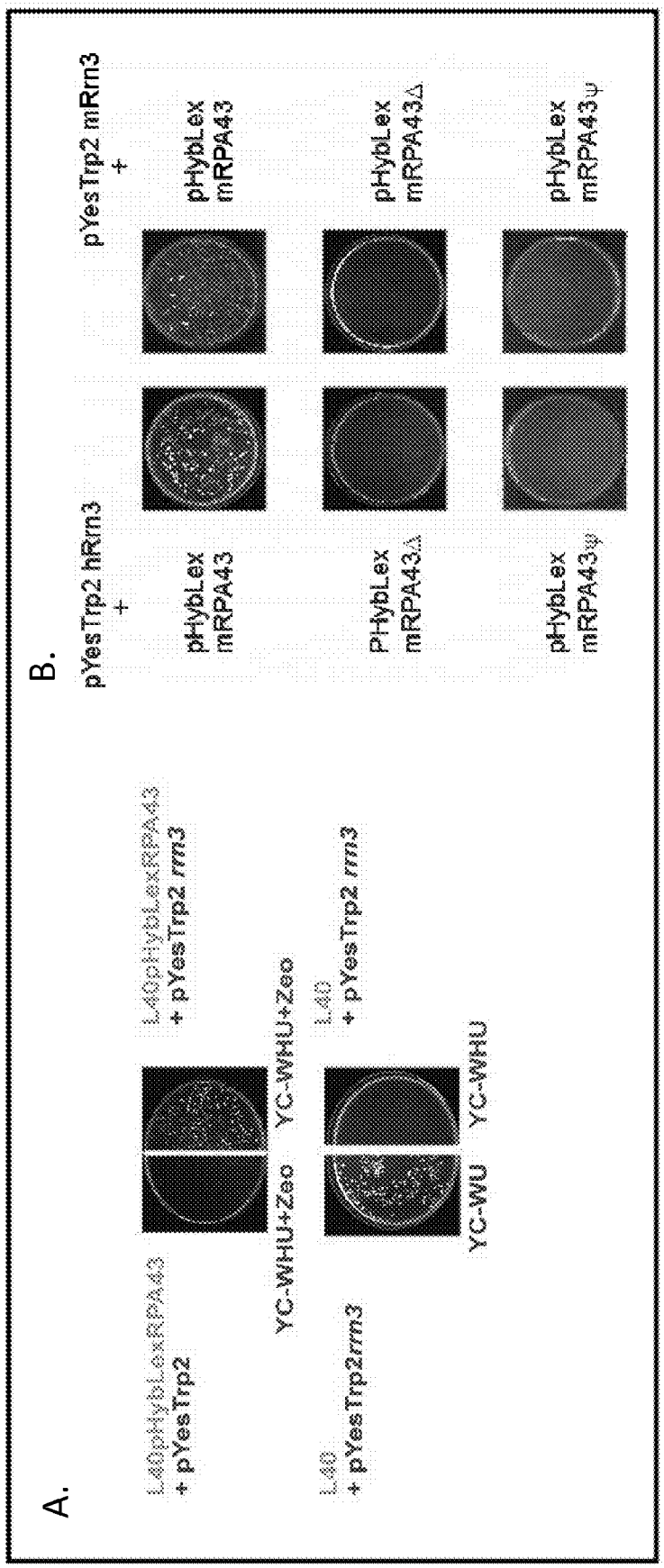
FIG. 3 contains the results of a two hybrid analysis that demonstrates that Rpa43 binds to Rrn3 (panel A), and that deletion (mRPA43Δ) or randomization (mRPA434Ψ) of the conserved domain alters the ability of Rpa43 to interact with either human Rrn3 (hRrn3) or mouse Rrn3 (mRrn3).

Before explaining at least one embodiment of the presently disclosed and claimed inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, biological chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, patent application publications and non-patent publications mentioned in the specification are indicative of the level of skill of those skilled in the art to which the presently disclosed and claimed inventive concept(s) pertains. All patents, patent application publications and non-patent publications are herein incorporated by reference to the same extent as if each individual patent or publication was specifically and individually indicated to be incorporated by reference.

All of the compositions and/or methods disclosed and claimed herein can be made and executed without undue experimentation in light of the present disclosure. While the compositions and methods of the presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The terms "peptide", "polypeptide" and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus. The term "isolated peptide/polypeptide/protein" as used herein refers to a peptide/polypeptide/protein of cDNA, recombinant RNA, or synthetic origin or some combination thereof, which by virtue of its origin, or source of derivation, the "isolated peptide/polypeptide/protein": (1) is not associated with peptides/polypeptides/proteins found in nature, (2) is free of other peptides/polypeptides/proteins from the same source, e.g., free of murine proteins, (3) is expressed by a cell from a different species, and/or (4) does not occur in nature.

As used herein, the term "amino acid" embraces all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The terms "polynucleotide", and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

The term "naturally-occurring" as used herein as applied to an object refers to the fact that an object can be found in nature. For example, a polynucleotide or polypeptide sequence that is present in an organism (including viruses) that can be isolated from a source in nature and which has not been intentionally modified by man in the laboratory or otherwise is naturally-occurring. The term "naturally-occurring" may be used interchangeably herein with the term "native".

The term "selectively hybridize" referred to herein means to detectably and specifically bind. Polynucleotides, oligonucleotides and fragments thereof encoding peptides/polypeptides/proteins in accordance with the inventive concept(s) selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the inventive concept(s) and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Adv. Appl. Math., 2:482 (1981)), by the homology alignment algorithm of Needleman and Wunsch (J. Mol. Biol., 48:443 (1970)), by the search for similarity method of Pearson and Lipman (Proc. Natl. Acad. Sci. (U.S.A.), 85:2444 (1988)), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages, or by inspection, and the best alignment (i.e., resulting in the highest percentage of homology over the comparison window) generated by the various methods is selected.

The term "sequence identity" means that two polynucleotide or amino acid sequences is identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the presently disclosed and claimed inventive concept(s). Examples of unconventional amino acids include: 4-hydroxyproline, α-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, such as at least 90 percent sequence identity, or at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "variant" of a reference polypeptide refers to a polypeptide having one or more amino acid substitutions, deletions or insertions relative to the reference polypeptide. An amino acid substitution may be "conservative" or "non-conservative". A "conservative" amino acid substitution refers to the substitution of an amino acid in a polypeptide with another amino acid having similar properties, such as but not limited to, size and charge. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., Science, 253:164 (1991)). Thus, the foregoing examples demonstrate that those of skill in the art can recognize sequence motifs and structural conformations that may be used to define structural and functional domains in accordance with the presently disclosed and claimed inventive concept(s).

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure© (Branden and J. Tooze, eds., Garland Publishing, New York, N.Y. (1991)); and Thornton et al. (Nature 354:105 (1991)), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence. A polypeptide fragment may be any length that is less than the length of the reference polypeptide.

The term "peptidomimetic" as used herein will be understood to refer to a compound containing non-peptidic structural elements that is capable of mimicking or antagonizing the biological action(s) of a natural parent peptide. The peptidomimetic compounds may be derived from peptides and proteins and may be obtained by structural modification thereof (such as but not limited to, the use of unnatural amino acids, conformational restraints, etc.).

As used herein, "substantially pure" means an object species is the predominant species present (i.e., on a molar basis it is more abundant than any other individual species in the composition). Generally, a substantially pure composition will comprise more than about 50% percent of all macromolecular species present in the composition, such as more than about 55%, 60%, 65%, 70%, 75%, 80%, 85%, 90%, 95%, and 99%. In one embodiment, the object species is purified to essential homogeneity (contaminant species cannot be detected in the composition by conventional detection methods) wherein the composition consists essentially of a single macromolecular species.

The term "patient" includes human and veterinary subjects. In certain embodiments, a patient is a mammal. In certain other embodiments, the patient is a human.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "disorder" is any condition that would benefit from treatment with the polypeptide. This includes chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

"Mammal" for purposes of treatment refers to any animal classified as a mammal, including human, domestic and farm animals, nonhuman primates, and zoo, sports, or pet animals, such as dogs, horses, cats, cows, etc.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting and/or neutralizing at least one activity of LRP6. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein The term "delivery vehicle" as used herein will be understood to refer to any molecule that assists in delivery of the compositions of the presently disclosed and claimed inventive concept(s) to a desired cell. Examples of delivery vehicles that may be utilized in accordance with the presently disclosed and claimed inventive concept(s) include, but are not limited to, liposomes, microspheres, nanoparticles and other nanoscale materials, polymer based delivery systems, and the like. The delivery vehicles utilized in accordance with the presently disclosed and claimed inventive concept(s) may be utilized alone or in combination with a targeting moiety.

The terms "targeting molecule" and "targeting moiety" are used interchangeably herein and will be understood to refer to any molecule/moiety that specifically recognizes a biomarker present on a cell to be targeted, thus directing the delivery of the compositions described herein to said cell. For example but not by way of limitation, targeting molecules that may be utilized in accordance with the presently disclosed and claimed inventive concept(s) include antibodies and antibody fragments, small and large molecule ligands of known receptors and antigens, and combinations thereof. Targeting molecules are well known in the art, and a person having ordinary skill in the art will readily understand how to select a particular targeting molecule and incorporate same into the compositions described herein; therefore, no further description of said targeting molecules is required.

As used herein, the term "concurrent therapy" is used interchangeably with the terms "combination therapy" and "adjunct therapy", and will be understood to mean that the patient in need of treatment is treated or given another drug for the disease/disorder in conjunction with the compositions of the presently disclosed and claimed inventive concept(s). This concurrent therapy can be sequential therapy where the patient is treated first with one drug and then the other, or the two drugs are given simultaneously The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The compositions of the presently disclosed and claimed inventive concept(s) may be administered to a patient by any method known in the art, including but not limited to, oral, topical, transdermal, parenteral, subcutaneous, intranasal, intramuscular, intraperitoneal, intravitreal and intravenous routes, including both local and systemic applications. In addition, the compounds of the presently disclosed and claimed inventive concept(s) may be designed to provide delayed, controlled or sustained release using formulation techniques which are well known in the art.

Turning now to the presently disclosed and claimed inventive concept(s), in one embodiment the inventive concept(s) is related to compositions comprising an isolated peptide having the sequence of at least one of SEQ ID NOS:1-174, or a fragment thereof. In certain embodiments, the isolated peptide may have a sequence of at least one of SEQ ID NOS:1-4, or a fragment thereof (i.e., at least one of SEQ ID NOS:5-174). Alternatively, the isolated peptide may have a sequence that is at least 80% identical to at least one of SEQ ID NOS:1-4, or at least 90% identical to at least one of SEQ ID NOS:1-4, or may contain five or less amino acid sequence changes (additions, deletions and/or substitutions) when compared to at least one of SEQ ID NOS:1-4, or may contain four or less amino acid sequence changes (additions, deletions and/or substitutions) when compared to at least one of SEQ ID NOS:1-4, or may contain three or less amino acid sequence changes (additions, deletions and/or substitutions) when compared to at least one of SEQ ID NOS:1-4, or may contain two or less amino acid sequence changes (additions, deletions and/or substitutions) when compared to at least one of SEQ ID NOS:1-4, may contain one amino acid sequence change (addition, deletion and/or substitution) when compared to at least one of SEQ ID NOS:1-4.

In certain, particular embodiments, the peptide fragment of the composition is 22-27 amino acids in length and comprises the sequence of: (i) one of SEQ ID NOS:1-3; (ii) $X_1X_2X_3X_4X_5X_6HX_8GX_{10}LX_{12}HGX_{15}X_{16}NASX_{20}PK$ (SEQ ID NO:4), wherein $X_1$ is N, F, or K; $X_2$ is K, R, L, or I; $X_3$ is V, Q, L, or M; $X_4$ is S, G, or A; $X_5$ is S, P, A, V, or T; $X_6$ is S or T; $X_8$ is I or V; $X_{10}$ is L or C; $X_{12}$ is V or I; $X_{15}$ is C, A, I, or T; $X_{16}$ is F or I; and $X_{20}$ is I or V; (iii) amino acids 6-27 of SEQ ID NO:179; (iv) amino acids 4-25 of SEQ ID NO:180; (v) amino acids 4-25 of SEQ ID NO:181; (vi) amino acids 4-25 of SEQ ID NO:182; (vii) amino acids 4-25 of SEQ ID NO:183; (viii) amino acids 3-24 of SEQ ID NO:184; (ix) amino acids 3-24 of SEQ ID NO:185; (x) amino acids 4-25 of SEQ ID NO:186; or (xi) amino acids 5-26 of SEQ ID NO: 187.

The composition may further include a tag to aid in cellular uptake (protein transduction domain) and/or monitor uptake (fluorescent tag—FITC). The composition may also include a delivery vehicle and/or a targeting moiety.

Another embodiment of the presently disclosed and claimed inventive concept(s) is also directed to an isolated DNA segment comprising a coding sequence encoding any of the compositions described herein above.

Yet another embodiment of the presently disclosed and claimed inventive concept(s) includes a recombinant vector comprising any of the isolated DNA segments described herein above.

A further embodiment of the presently disclosed and claimed inventive concept(s) includes a recombinant host cell comprising any of the recombinant vectors described herein above. In certain embodiments, the recombinant host cell produces one or more of the peptide compositions described herein above.

In another embodiment, the presently disclosed and claimed inventive concept(s) is directed to a peptidomimetic designed to mimic at least one of the peptide compositions described herein above. As disclosed herein, a peptidomimetic is a peptide equivalent characterized as retaining the polarity, three dimensional size and/or functionality (bioactivity) of its peptide equivalent but where the peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include, but are not limited to, the following groups: N-alkylation (Schmidt, R. et. al., Int. J. Peptide Protein Res., 1995, 46, 47), retro-inverse amide (Chorev, M. and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391); each of the above-listed references is incorporated herein by reference in its entirety.

The presently disclosed and claimed inventive concept(s) also includes a pharmaceutical composition comprising any of the peptides described herein above, or an active peptidomimetic thereof. In certain embodiments, the pharmaceutical composition may be for inhibiting rDNA transcription and/or synthesis of 45S pre-ribosomal RNA, wherein the peptide/peptidomimetic inhibits interaction of Rrn3 and Rpa43.

Yet another embodiment of the presently disclosed and claimed inventive concept(s) includes a method of inhibiting interaction of Rrn3 and Rpa43. Said method may include administering at least one of the compositions described herein above to a cell and/or introducing at least one of the recombinant vectors described herein above into a cell.

Another embodiment of the presently disclosed and claimed inventive concept(s) is directed to a method of inhibiting synthesis of 45S pre-ribosomal RNA. Said method may include administering at least one of the compositions described herein above to a cell and/or introducing at least one of the recombinant vectors described herein above into a cell.

Another embodiment of the presently disclosed and claimed inventive concept(s) is directed to a method of inhibiting rDNA transcription. Said inhibition may occur via inhibition of the interaction between Rpa43 and Rrn3. Said method may include administering at least one of the compositions described herein above to a cell and/or introducing at least one of the recombinant vectors described herein above into a cell.

Yet another embodiment of the presently disclosed and claimed inventive concept(s) is directed to a method of inhibiting cell growth. Said method may include administering at least one of the compositions described herein above to a cell and/or introducing at least one of the recombinant vectors described herein above into a cell.

TABLE 1

| SEQ ID NO: | Amino Acid Sequence | |
|---|---|---|
| 1 | NKVSSSHIGCLVHGCFNASIPK | |
| 2 | NKVSSSHIGXLVHGXFNASIPK | wherein X is any amino acid except Cys |
| 3 | NKVSSSHIGSLVHGSFNASIPK | serines substituted for Cys as in SEQ ID NO: 3 |
| 4 | XxXXxXHXGXLXHGXXNASXPK | Consensus sequence: Where $X_1$ = N, F, or K; $X_3$ = V, Q, L, or M; $X_4$ = S, G, or A; $X_6$ = S or T; $X_8$ = I or V; $X_{10}$ = L or C; $X_{12}$ = V or I; $X_{15}$ = C, A, I, or T; $X_{16}$ = F or I; $X_{20}$ = I or V |

TABLE 2

Amino Acid Sequences of Fragments
(*X may be any amino acid)

| SEQ ID NO: | Amino Acid Sequence |
|---|---|
| 5 | NKVSS |
| 6 | KVSSS |
| 7 | VSSSH |
| 8 | SSSHI |
| 9 | SSHIG |
| 10 | SHIGX |
| 11 | HIGXL |
| 12 | IGXLV |
| 13 | GXLVH |
| 14 | XLVHG |
| 15 | LVHGX |
| 16 | VHGXF |
| 17 | HGXFN |
| 18 | GXFNA |
| 19 | XFNAS |
| 20 | FNASI |
| 21 | NASIP |
| 22 | ASIPK |
| 23 | NKVSSS |
| 24 | KVSSSH |
| 25 | VSSSHI |
| 26 | SSSHIG |

TABLE 2-continued

Amino Acid Sequences of Fragments
(*X may be any amino acid)

| SEQ ID NO: | Amino Acid Sequence |
|---|---|
| 27 | SSHIGX |
| 28 | SHIGXL |
| 29 | HIGXLV |
| 30 | IGXLVH |
| 31 | GXLVHG |
| 32 | XLVHGX |
| 33 | LVHGXF |
| 34 | VHGXFN |
| 35 | HGXFNA |
| 36 | GXFNAS |
| 37 | XFNASI |
| 38 | FNASIP |
| 39 | NASIPK |
| 40 | NKVSSSH |
| 41 | KVSSSHI |
| 42 | VSSSHIG |
| 43 | SSSHIGX |
| 44 | SSHIGXL |
| 45 | SHIGXLV |
| 46 | HIGXLVH |
| 47 | IGXLVHG |
| 48 | GXLVHGX |
| 49 | XLVHGXF |
| 50 | LVHGXFN |
| 51 | VHGXFNA |
| 52 | HGXFNAS |
| 53 | GXFNASI |
| 54 | XFNASIP |
| 55 | FNASIPK |
| 56 | NKVSSSHI |
| 57 | KVSSSHIG |
| 58 | VSSSHIGX |
| 59 | SSSHIGXL |
| 60 | SSHIGXLV |
| 61 | SHIGXLVH |
| 62 | HIGXLVHG |
| 63 | IGXLVHGX |
| 64 | GXLVHGXF |
| 65 | XLVHGXFN |
| 66 | LVHGXFNA |
| 67 | VHGXFNAS |
| 68 | HGXFNASI |
| 69 | GXFNASIP |
| 70 | XFNASIPK |
| 71 | NKVSSSHIG |
| 72 | KVSSSHIGX |
| 73 | VSSSHIGXL |
| 74 | SSSHIGXLV |
| 75 | SSHIGXLVH |
| 76 | SHIGXLVHG |
| 77 | HIGXLVHGX |
| 78 | IGXLVHGXF |
| 79 | GXLVHGXFN |
| 80 | XLVHGXFNA |
| 81 | LVHGXFNAS |
| 82 | VHGXFNASI |
| 83 | HGXFNASIP |
| 84 | GXFNASIPK |
| 85 | NKVSSSHIGX |
| 86 | KVSSSHIGXL |
| 87 | VSSSHIGXLV |
| 88 | SSSHIGXLVH |
| 89 | SSHIGXLVHG |
| 90 | SHIGXLVHGX |
| 91 | HIGXLVHGXF |
| 92 | IGXLVHGXFN |
| 93 | GXLVHGXFNA |
| 94 | XLVHGXFNAS |
| 95 | LVHGXFNASI |
| 96 | VHGXFNASIP |
| 97 | HGXFNASIPK |
| 98 | NKVSSSHIGXL |
| 99 | KVSSSHIGXLV |
| 100 | VSSSHIGXLVH |
| 101 | SSSHIGXLVHG |

TABLE 2-continued

Amino Acid Sequences of Fragments
(*X may be any amino acid)

| SEQ ID NO: | Amino Acid Sequence |
|---|---|
| 102 | SSHIGXLVHGX |
| 103 | SHIGXLVHGXF |
| 104 | HIGXLVHGXFN |
| 105 | IGXLVHGXFNA |
| 106 | GXLVHGXFNAS |
| 107 | XLVHGXFNASI |
| 108 | LVHGXFNASIP |
| 109 | VHGXFNASIPK |
| 110 | NKVSSSHIGXLV |
| 111 | KVSSSHIGXLVH |
| 112 | VSSSHIGXLVHG |
| 113 | SSSHIGXLVHGX |
| 114 | SSHIGXLVHGXF |
| 115 | SHIGXLVHGXFN |
| 116 | HIGXLVHGXFNA |
| 117 | IGXLVHGXFNAS |
| 118 | GXLVHGXFNASI |
| 119 | XLVHGXFNASIP |
| 120 | LVHGXFNASIPK |
| 121 | NKVSSSHIGXLVH |
| 122 | KVSSSHIGXLVHG |
| 123 | VSSSHIGXLVHGX |
| 124 | SSSHIGXLVHGXF |
| 125 | SSHIGXLVHGXFN |
| 126 | SHIGXLVHGXFNA |
| 127 | HIGXLVHGXFNAS |
| 128 | IGXLVHGXFNASI |
| 129 | GXLVHGXFNASIP |
| 130 | XLVHGXFNASIPK |
| 131 | NKVSSSHIGXLVHG |
| 132 | KVSSSHIGXLVHGX |
| 133 | VSSSHIGXLVHGXF |
| 134 | SSSHIGXLVHGXFN |
| 135 | SSHIGXLVHGXFNA |
| 136 | SHIGXLVHGXFNAS |
| 137 | HIGXLVHGXFNASI |
| 138 | IGXLVHGXFNASIP |
| 139 | GXLVHGXFNASIPK |
| 140 | NKVSSSHIGXLVHGX |
| 141 | KVSSSHIGXLVHGXF |
| 142 | VSSSHIGXLVHGXFN |
| 143 | SSSHIGXLVHGXFNA |
| 144 | SSHIGXLVHGXFNAS |
| 145 | SHIGXLVHGXFNASI |
| 146 | HIGXLVHGXFNASIP |
| 147 | IGXLVHGXFNASIPK |
| 148 | NKVSSSHIGXLVHGXF |
| 149 | KVSSSHIGXLVHGXFN |
| 150 | VSSSHIGXLVHGXFNA |
| 151 | SSSHIGXLVHGXFNAS |
| 152 | SSHIGXLVHGXFNASI |
| 153 | SHIGXLVHGXFNASIP |
| 154 | HIGXLVHGXFNASIPK |
| 155 | NKVSSSHIGXLVHGXFN |
| 156 | KVSSSHIGXLVHGXFNA |
| 157 | VSSSHIGXLVHGXFNAS |
| 158 | SSSHIGXLVHGXFNASI |
| 159 | SSHIGXLVHGXFNASIP |
| 160 | SHIGXLVHGXFNASIPK |
| 161 | NKVSSSHIGXLVHGXFNA |
| 162 | KVSSSHIGXLVHGXFNAS |
| 163 | VSSSHIGXLVHGXFNASI |
| 164 | SSSHIGXLVHGXFNASIP |
| 165 | SSHIGXLVHGXFNASIPK |
| 166 | NKVSSSHIGXLVHGXFNAS |
| 167 | KVSSSHIGXLVHGXFNASI |
| 168 | VSSSHIGXLVHGXFNASIP |
| 169 | SSSHIGXLVHGXFNASIPK |
| 170 | NKVSSSHIGXLVHGXFNASI |
| 171 | KVSSSHIGXLVHGXFNASIP |
| 172 | VSSSHIGXLVHGXFNASIPK |
| 173 | NKVSSSHIGXLVHGXFNASIP |
| 174 | KVSSSHIGXLVHGXFNASIPK |

Examples are provided hereinbelow. However, the present inventive concept(s) is to be understood to not be limited in its application to the specific experimentation, results and laboratory procedures. Rather, the Examples are simply provided as one of various embodiments and are meant to be exemplary, not exhaustive.

Example 1

In all organisms studied so far, the productive recruitment of RNA polymerase I to the 45S rDNA promoter requires an interaction between the transcription factor(s) bound to the promoter and RNA polymerase I. The Rrn3 protein (referred to as Rrn3p in yeast) serves, at least in part, as the mediator of that interaction (FIG. 1). In the absence of Rrn3, RNA polymerase I is recruited to a nonproductive complex and does not initiate transcription. As mentioned Rrn3 interacts with both the core factor(s) and RNA polymerase I. In fact, it interacts with a 43 kDa subunit of RNA polymerase I referred to herein as Rpa43. In this Example, the interaction between Rrn3 and RNA polymerase I has been evaluated, and a "conserved" 22 amino acid long segment of Rpa43 has been identified (FIG. 2). In order to analyze the function of this domain, both deletion and substitution mutants of this domain were created. These mutants were first analyzed in a two-hybrid assay to determine if the interaction between Rrn3 and Rpa43 was affected by the mutations (FIG. 3). The two-hybrid analysis demonstrated that Rpa43 binds to Rrn3 (Panel A); further, the analysis demonstrated that deletion (mRPA43Δ) or randomization (mRPAΨ) of the 22 amino acids altered the ability of Rpa43 to interact with either human Rrn3 (hRrn3) or mouse Rrn3 (mRrn3).

Figure 4:
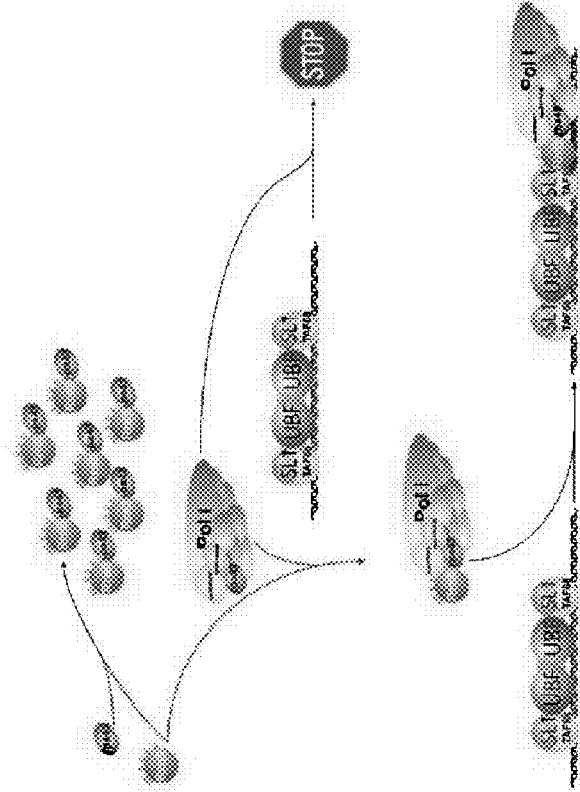
FIG. 4 graphically depicts that the composition of the currently disclosed and claimed inventive concept(s) is sufficient to mediate interaction between Rpa43 and Rrn3. Immunoaffinity purified Rrn3 was incubated with streptavidin beads that had been preincubated with biotin-tagged 22mer or control extracts. After the beads were washed the proteins bound to the beads were analyzed by SDS-PAFE and western blotting for Rrn3 (anti-FLAG antibody).

These results suggested that it might be possible to squelch or inhibit rDNA transcription by adding an excess of either Rpa43, or a peptide fragment containing the 22mer, to a transcription reaction. A cartoon depicting this model is presented in FIG. 4.

Figure 6:
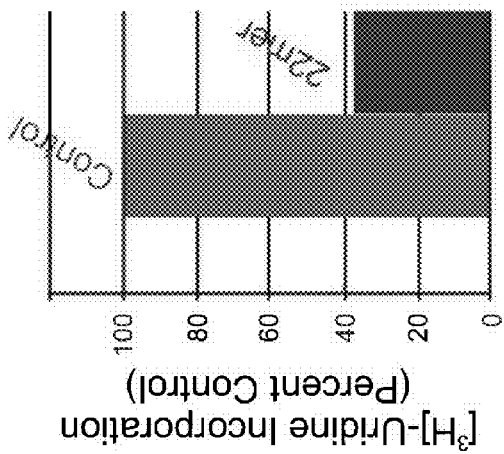
FIG. 6 illustrates squelching by excess Rpa43 or the peptide (22mer) that mediates the interaction between Rpa43 and Rrn3. Panel A. The addition of excess, free Rpa43 (lanes 4 and 5) to a cell-free transcription reaction inhibits transcription, but not the mutant with the randomized binding site (Ψ Rpa43) that cannot interact with Rrn3. Panel B. The addition of the 22mer inhibits transcription (lanes 3-5), but the addition of randomized peptide (Ψ) does not (lanes 6-9).

To test this model, recombinant Rpa43 was purified and added to cell free transcription reactions to determine if excess Rpa43 could inhibit transcription. The components added to this reaction included nuclear extracts of N1S1 cells (a rat tumor cell line), and recombinant DNA of the rat rDNA promoter and the purified, recombinant Rpa43 or purified synthetic peptides (FIG. 6). As shown in FIG. 6, Panel A, the addition of wild type Rpa43 inhibited transcription (lanes 4 and 5), while the addition of equal amounts of the mutant form of Rpa43 (Ψ Rpa43), which does not bind to Rrn3, did not inhibit transcription (lanes 2 and 3). A similar series of experiments was then undertaken with synthetic peptides. The two peptides were based on the sequence of the region shown to be required for the interaction between Rrn3 and Rpa43 (FIG. 6, Panel B). When the peptide with the same sequence of Rpa43 (22mer, i.e., SEQ ID NO:1) was added to the transcription reaction, transcription was inhibited (lanes 2-5). However, the addition of the peptide with the randomized sequence (Ψ peptide) had no effect on rDNA transcription (lanes 6-9).

Figure 7:
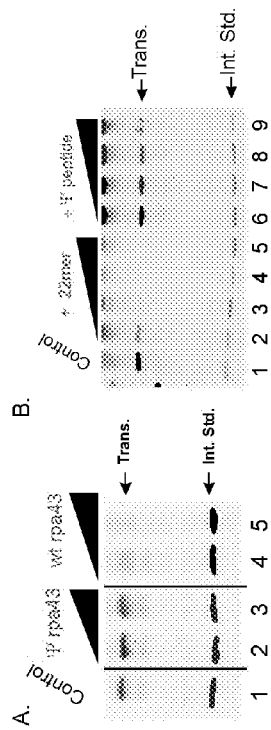
FIG. 7 illustrates that transduction of the 22mer inhibits rDNA transcription in tissue culture cells. Low density cultures of N1S1 cells were transduced with the TAT-22mer (40 μM). Eight hours after transduction, the cells were incubated with tritiated uridine to label newly synthesized RNA. Total RNA was precipitated with TCA and collected on glass fiber filters, and the radioactivity incorporated was measured by liquid scintillation counting. Treatment with the peptide resulted in a 70% inhibition of [$^3$H]-uridine incorporation or nearly 100% inhibition of rDNA transcription.

These data were consistent with the model presented herein that excess Rpa43 or fragments thereof (i.e., merely that portion of Rpa43 that interacted with Rrn3) could block rDNA transcription in vitro. This effect was then tested in vivo, i.e. with immortalized cells in tissue culture. There are several possible ways of introducing the desired peptide into cells. In a first experiment, ten amino acids, YGRKKE-EQRR (SEQ ID NO:176), were added to the N-terminus of the 22mer peptide, NKVSSSHIGCLVHGCFNASIPK (resulting in a sequence of YGRKKEEQRRNKVSSSHIG-CLVHGCFNASIPK (SEQ ID NO:175)); the ten amino acids were added to assist in transduction of the peptide into the cells. The TAT peptide is an NH2-terminal 11-amino acid protein transduction domain (PTD) from the human immunodeficiency virus (HIV) TAT protein that was first identified in 1988 by Green et al. This peptide and peptides like it are capable of transducing proteins across the cell membrane. When exponentially growing, N1S1 cells were treated with the TAT-22mer peptide, cell growth was inhibited, as would be expected if rRNA synthesis were inhibited (FIG. 7).

Figure 8:
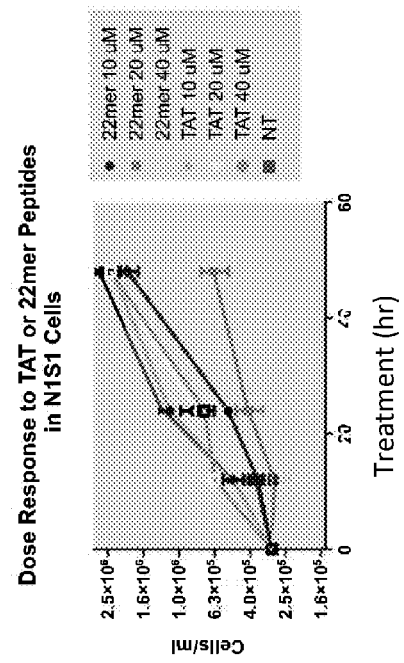
FIG. 8 illustrates that expression of the 22mer inhibits cell growth in comparison to the expression of the pseudo peptide (Ψ).

To confirm and extend these studies, cell lines were constructed that were based on 293T cells (Invitrogen, Carlsbad, Calif.), that expressed doxycycline-inducible 22mer or the random peptide (Ψ). There was a significant decrease in the rate of cell division in the cells expressing the 22mer versus those expressing the Ψ peptide when the cells were grown in doxycycline (FIG. 8). N.B., there was an inhibition of growth.

Figure 9:
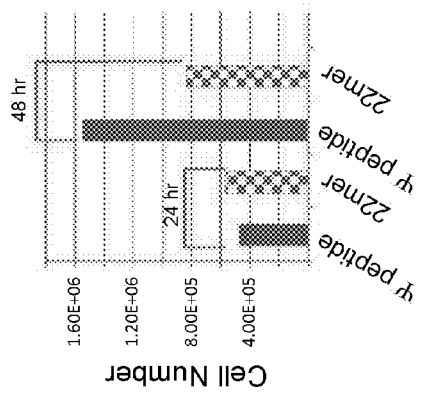
FIG. 9 illustrates that transduction of N1S1 hepatoma cells with the 22mer inhibits cell division in comparison to the transduction with either the TAT peptide alone (TAT) or untreated cells (NT). Note the decreased rate of cell accumulation following treatment with 20 and 40 μM 22mer.

The effects of transducing the 22mer coupled to TAT peptide were then compared to TAT peptide alone. An aggressive chemically-induced hepatoma cell line (N1S1 cells) was used for these experiments. As shown in FIG. 9, the 22mer significantly inhibited cell growth in a dose-dependent manner. After 48 hr, the cells cultured in the presence of 40 μM 22mer appeared to be apoptotic. These results demonstrated that the endpoint of treatment may be cell death.

Example 2

Example 1 demonstrated that the amino acids from 137 to 158 of mouse Rpa43 were highly conserved in eukaryotes (referred to as the 22mer or as Stopbaby (STBY)). In fact, these sequences are 100% conserved in the human, rat and mouse forms of Rpa43. When this region of mouse Rpa43 was mutated, the protein no longer interacted with Rrn3. Hence, this region was necessary for the interaction between Rpa43 and Rrn3. In this Example, it was evaluated whether or not this 22 amino acid long region of Rpa43 was sufficient for the interaction with Rrn3.

Figure 5:
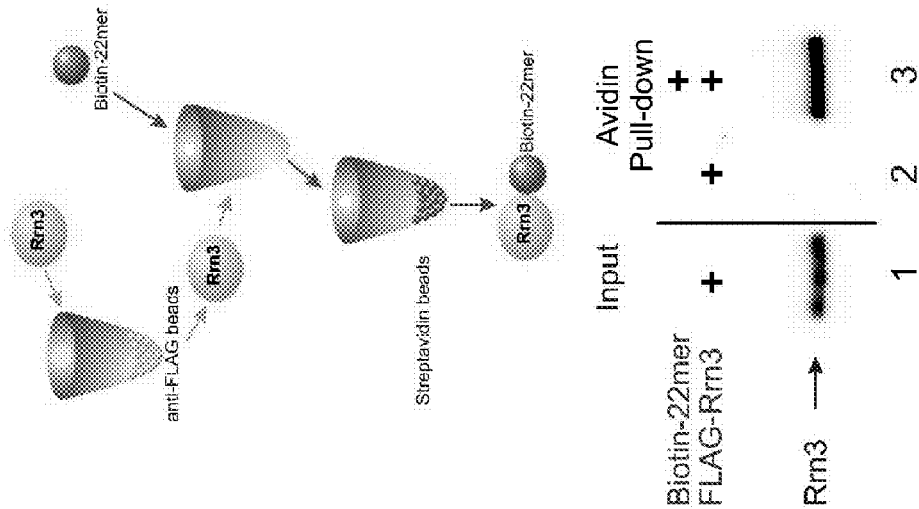
FIG. 5 illustrates squelching by excess Rpa43. This cartoon depicts the interactions of Rrn3/free Rpa43 and RNA polymerase I. In the presence of excess, free Rpa43 (i.e., Rpa43 that is not associated with pol I), Rrn3 forms a complex with the free Rpa43 and not with RNA polymerase I. Under these conditions, RNA polymerase I would be incapable of initiating transcription.

In order to address that question, a biotinylated peptide made up of those 22 amino acids (biotin-NKVSSSHIG-CLVHGCFNASIPK (SEQ ID NO:1)) was attached to streptavidin beads, and the ability to bind purified, recombinant Rrn3 was determined. As shown in FIG. 5, the Rrn3 bound to beads containing the biotinylated 22mer (lane 3). In contrast, Rrn3 did not bind to naked streptavidin beads (lane 2). From these results, and those obtained with the deletion mutants of Rpa43, it was concluded that the 22 amino acid segment of mouse (and human and rat) Rpa43 is both necessary and sufficient for the interaction with Rrn3.

The addition of TAT-tagged 22mer (SEQ ID NO:175) inhibited the growth of transformed cells in tissue culture (as described in detail herein below). However, it was possible that the same peptide would inhibit the growth of "normal" cells as well. To examine this possibility, TAT-tagged 22mer was added to the media of NIH 3T3 cells, and growth was measured after 48 hours.

Figure 12:
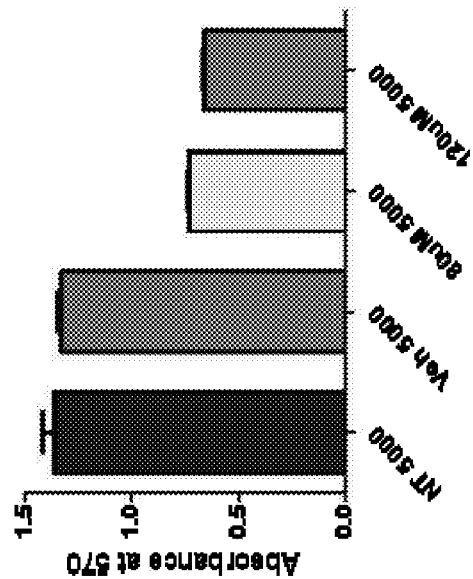
FIG. 12 illustrates the effects of TAT-22mer on the growth of A431 cells plated at low density after 72 hr.
Figure 10:
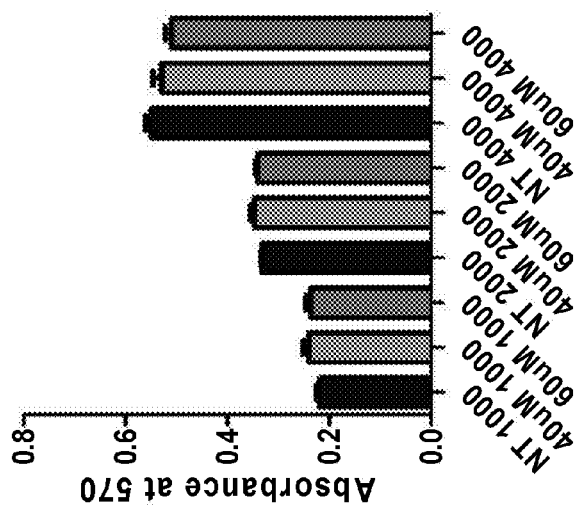
FIG. 10 illustrates the effects of a TAT-tagged 22mer (TAT-22mer) composition of the presently disclosed inventive concept(s) on NIH 3T3 cells plated at three different densities after 48 hours.
Figure 11B:
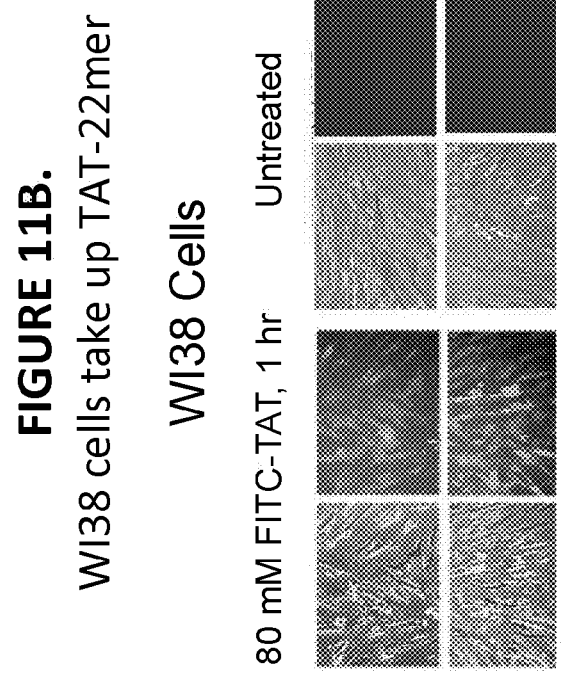
FIG. 11 illustrates the effects of TAT-22mer on WI38 cells after 48 hours using the MTT assay. Panel 11A demonstrates a minimal effect on cell accumulation. Panel 11B demonstrates that the cells take up fluorescent TAT-tagged 22mer.
Figure 11A:
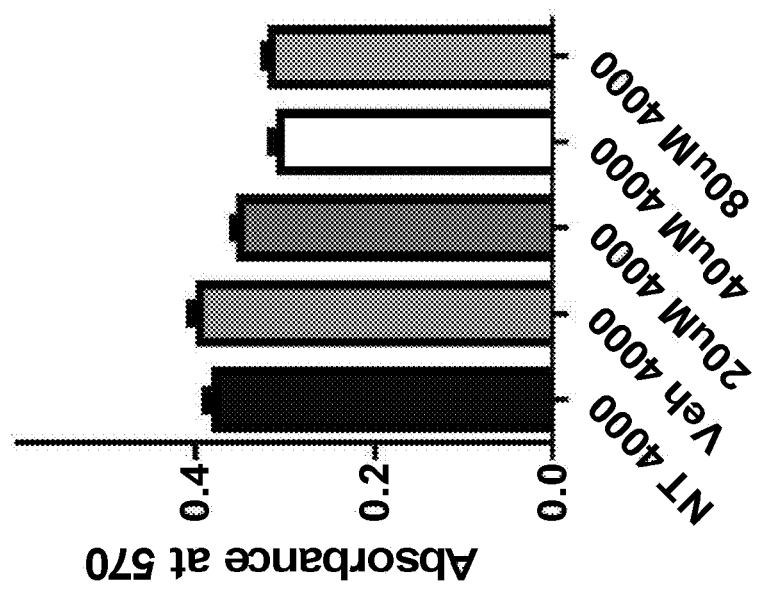

As shown in FIG. 10, the 22mer had no effects on the growth of 3T3 cells at 48 hours when the cells were plated at either of three densities or treated with two different concentrations of the 22mer (40 and 60 μM). Similarly, the 22mer had a minimal effect on the growth of WI38 cells (FIG. 11), although they did take up the peptide (FIG. 11B). In contrast, the peptide inhibited the growth of slowly growing A431 cells (FIG. 12). In these experiments, and in others described below, cell numbers were determined using the MU assay, and the absorbance at 570 nm is presented instead of cell numbers.

Figure 13:
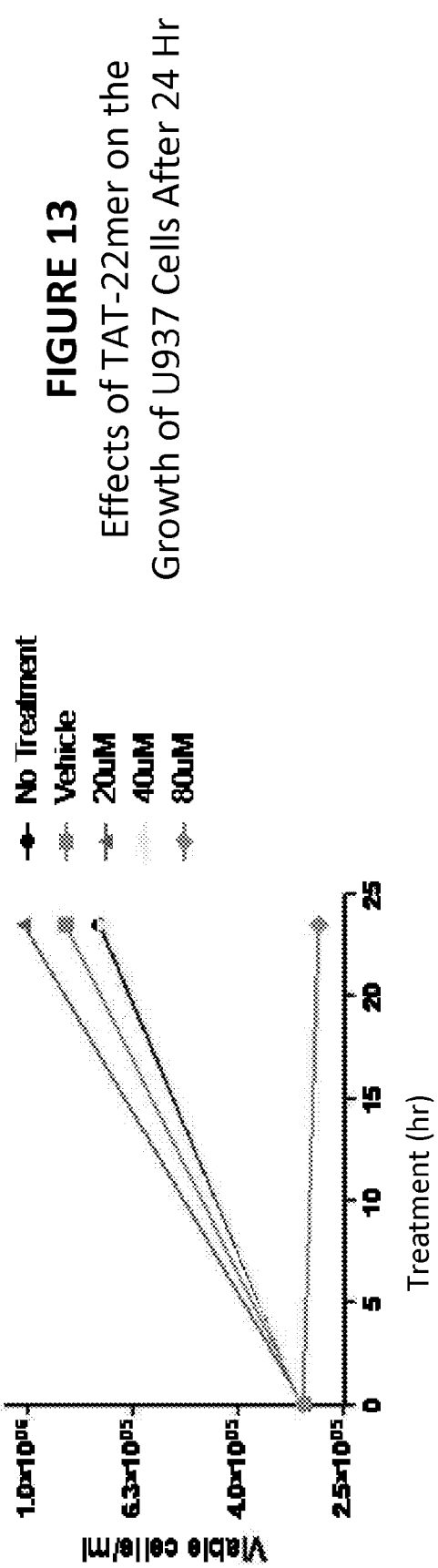
FIG. 13 illustrates the effects of TAT-22mer on the growth of U937 cells after 24 hours. Note the significant inhibition of cell growth when the cells were treated with 80 μM 22mer.
Figure 14:
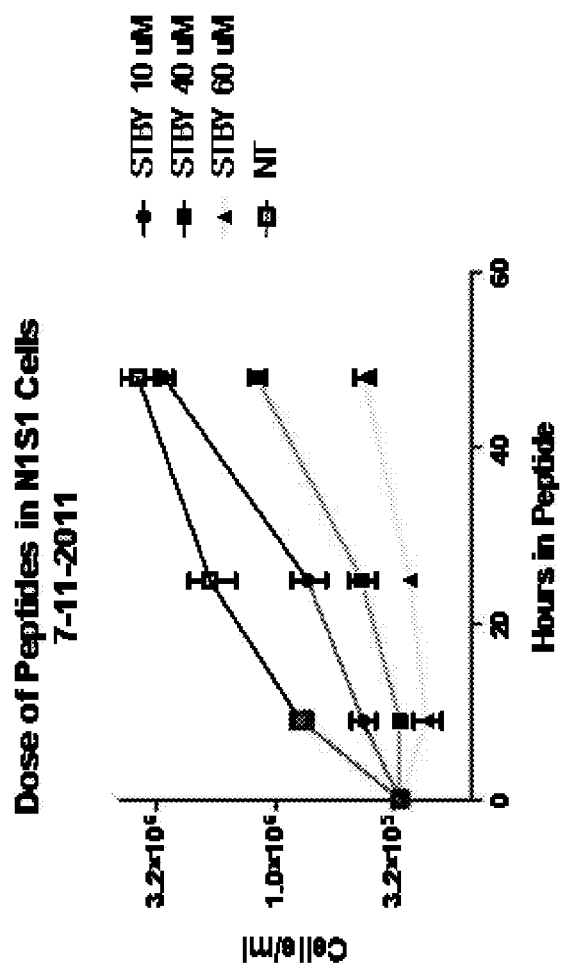
FIG. 14 illustrates the effects of TAT-22mer (labeled "STBY") on the growth of N1S1 rat hepatoma cells.
Figure 16:
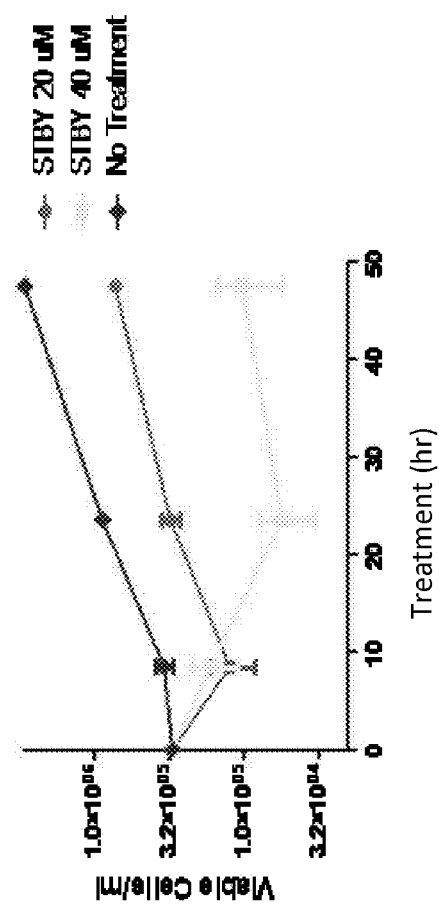
FIG. 16 illustrates the effect of TAT-22mer on P1798 mouse lymphosarcoma cells.
Figure 17:
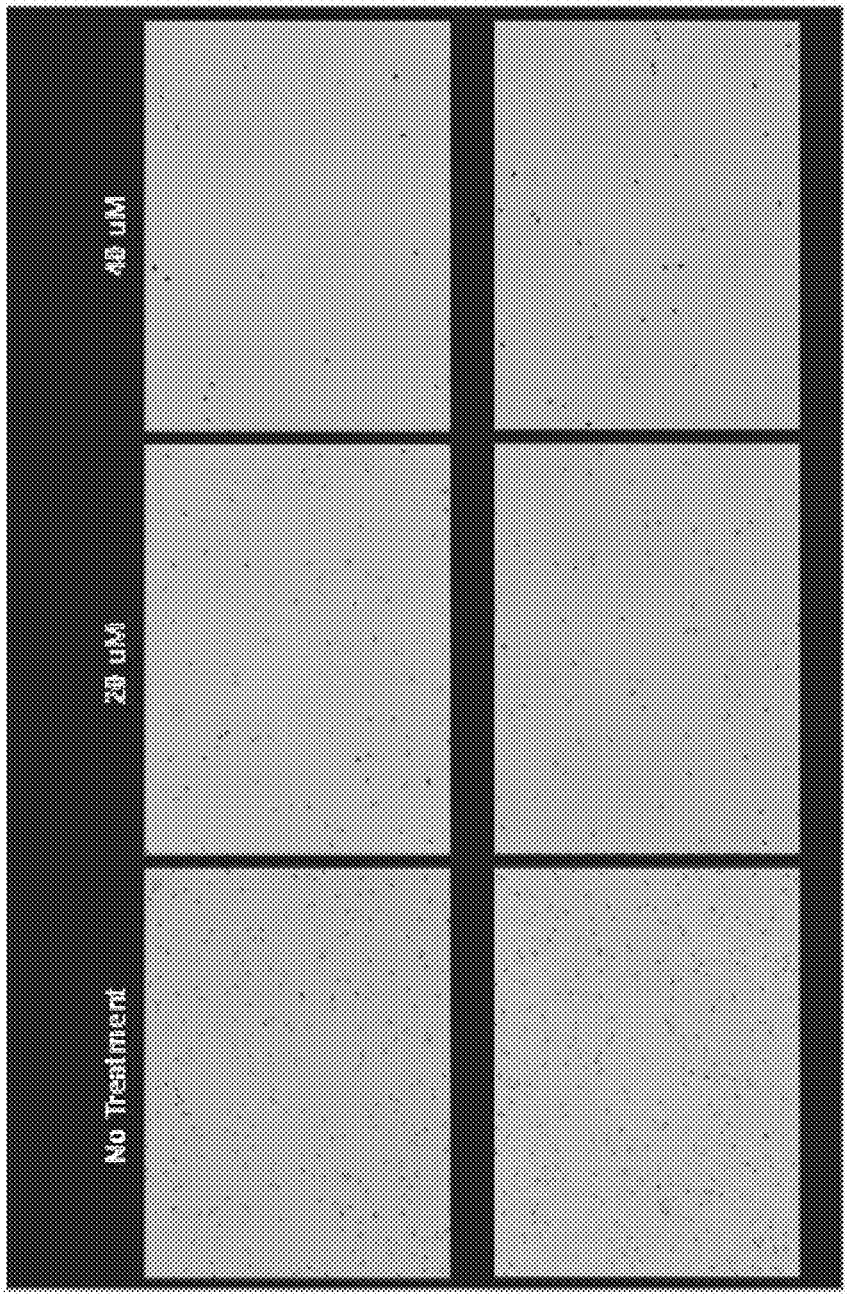
FIG. 17 contains micrographs of P1798 mouse lymphosarcoma cells treated with TAT-22mer ("STBY peptide") at indicated doses. The cells were stained with trypan blue to determine viability. Note that most of the cells treated with 40 µM STBY did not exclude the dye.

In contrast to the results obtained with "normal" cells (NIH 3T3 or WI38), the peptide (referred to as "STBY") had very significant effects on the growth of U937 human lymphoma cells (FIG. 13), N1S1 rat hepatoma cells (FIG. 14) and P1798 mouse lymphosarcoma cells (FIG. 16). As shown in the photomicrographs in FIG. 17, the treatment of P1798 cells significantly reduced the number of viable cells.

The peptide had a very significant effect on the P1798 cells (FIG. 16)—note that the cells demonstrate a significant response at a dose of 40 micromolar. Analysis of the experiment indicated that those cells were grown in a reducing medium. When the sequence of the 22mer was examined, it was noted that it contains two cysteine residues that might form a disulfide bond and inhibit the activity of the peptide. To examine this question, the experiment previously carried out on the N1S1 cells was repeated using peptide that was dissolved in 0.1 mM DU.

Figure 15:
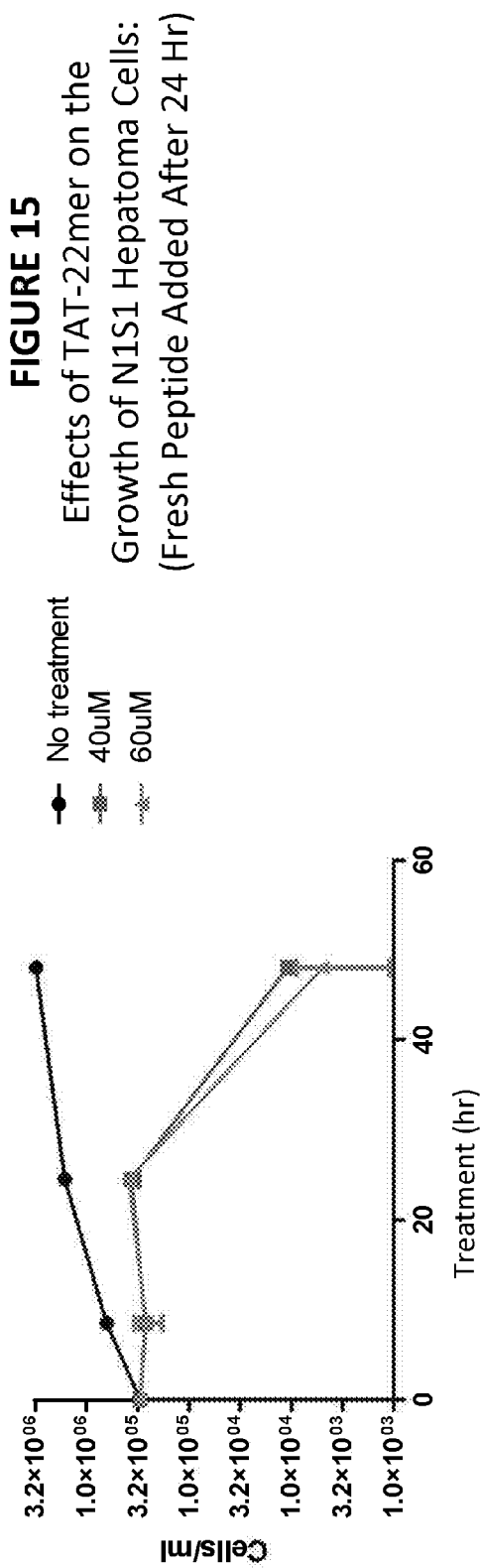
FIG. 15 illustrates the effects of TAT-22mer (labeled "STBY") on the growth of N1S1 rat hepatoma cells (fresh peptide added after 24 hours).

As shown in FIG. 15, the dissolution of the peptide in a low concentration of a reducing agent (dithiothreitol, DU) significantly increased the efficacy of the peptide. The N1S1 cells not only failed to grow, but the treated cells decreased in number by 90%.

Example 3

Figure 18:
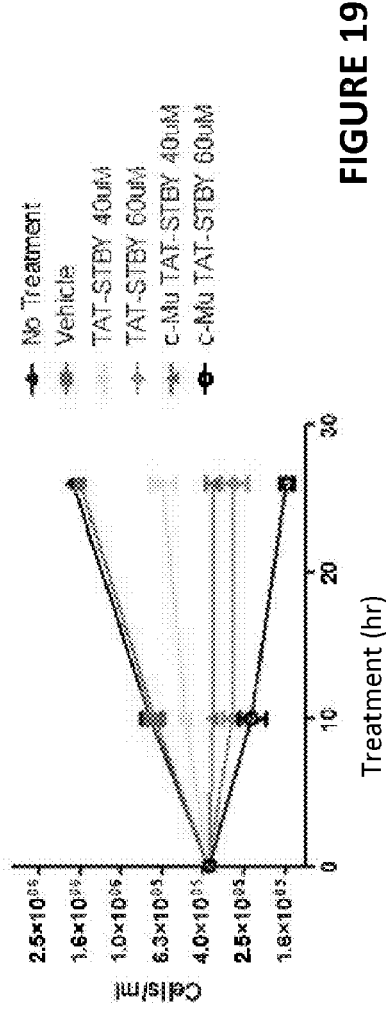
FIG. 18 illustrates the effects of TAT-22mer (TAT-STBY) and TAT-STBY C-Mu on P1798 mouse lymphosarcoma cells. TAT-STBY C-Mu was more effective at inhibiting cell growth than TAT-STBY.
Figure 19:
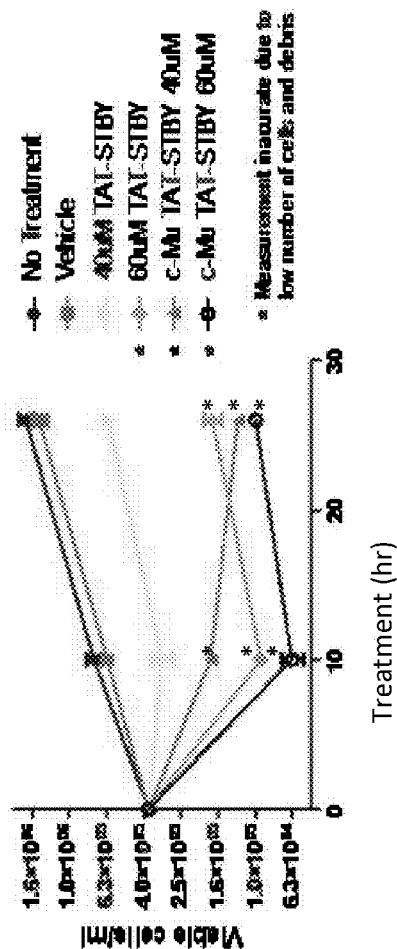
FIG. 19 illustrates the effects of TAT-22mer (TAT-STBY) and TAT-STBY C-Mu on the viability of P1798 mouse lymphosarcoma cells. The same cells studied in the experiment presented in FIG. 18, were also stained with Trypan blue to determine viability. The viable cell counts at 10 and 24 hrs of treatment were too low to be considered reliable (*).
Figure 21:
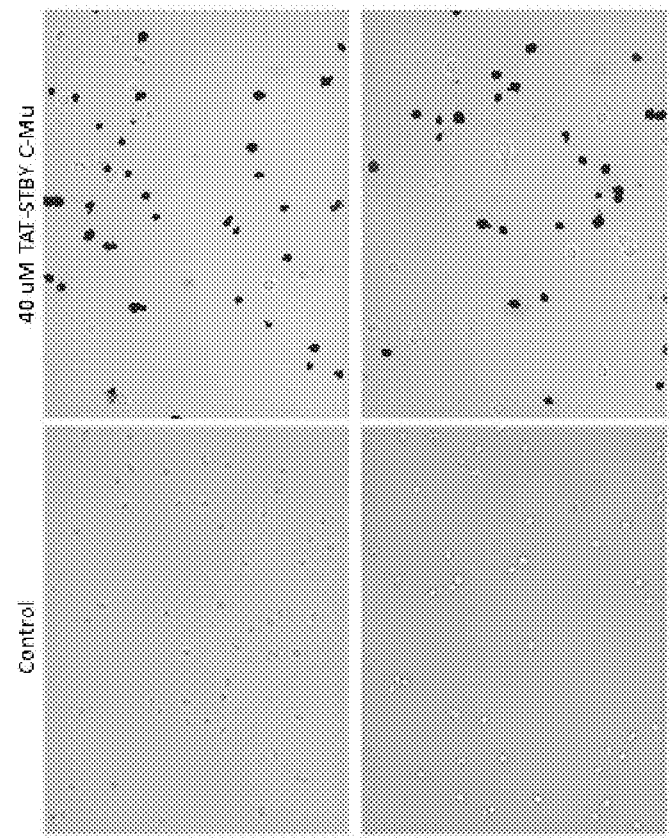
FIG. 21 illustrates the effects of TAT-22mer (TAT-STBY) and TAT-STBY C-Mu on P1798 mouse lymphosarcoma cells. P1798 Cells were treated with TAT-STBY C-Mu for 26 hours and then stained with Trypan blue. Note the high proportion of Trypan blue stained cells. The treated cells were concentrated 20× for photography.
Figure 20:
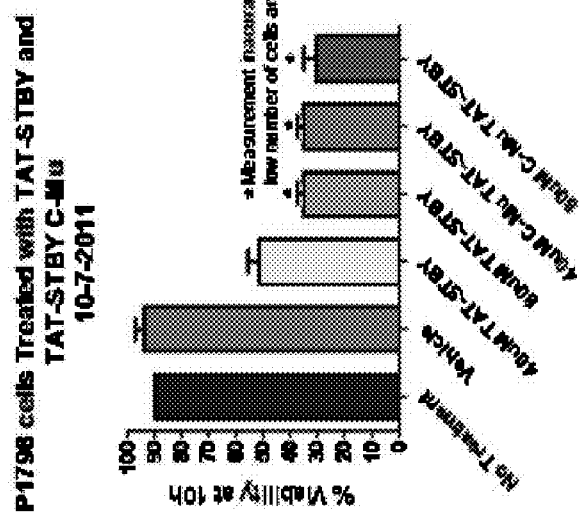
FIG. 20 illustrates the effects of TAT-22mer (TAT-STBY) and TAT-STBY C-Mu on the viability of P1798 mouse lymphosarcoma cells as analyzed in FIGS. 18 and 19.
Figure 22:
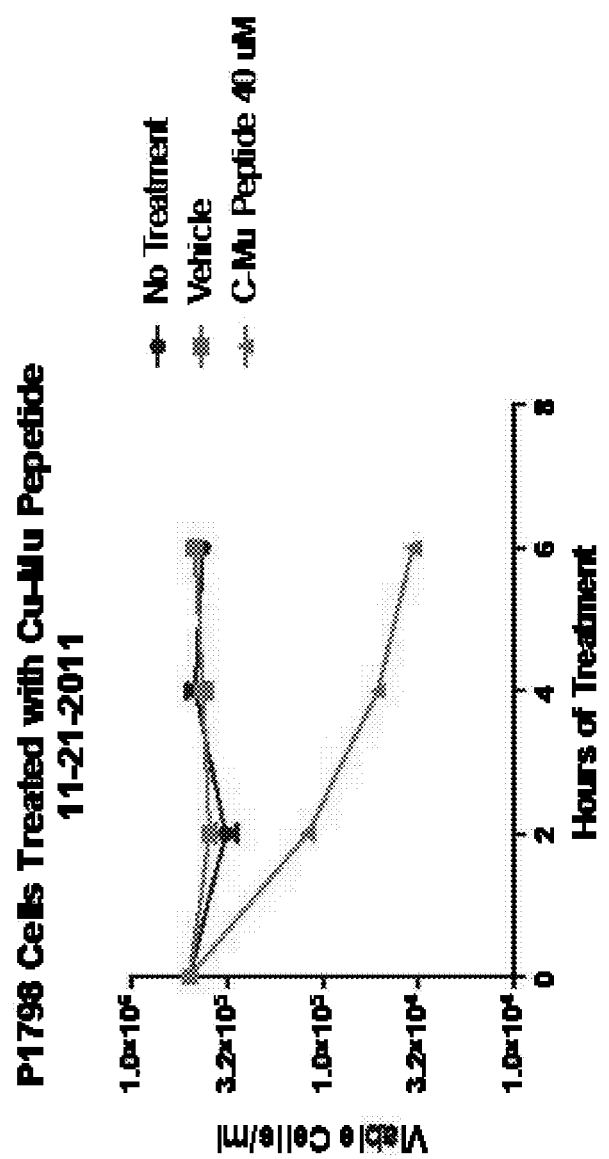
FIG. 22 illustrates the kinetics of cell death following treatment with C-Mu peptide. P1798 cells were treated with 40 mM C-Mu peptide. Cells were harvested by centrifugation every two hours, and the numbers of viable cells were determined using the Trypan blue exclusion assay.

The experiments with reducing agent suggested that the presence of the two cysteines in the 22mer could result in the formation of intramolecular disulfide bonds that inhibited its activity. This in turn suggested that the peptide might be more active if one or both of those cysteines were mutated to another amino acid. Hence, a serine was substituted for amino acid 10 of the 22mer. When P17908 cells were treated with this peptide, referred to as TAT-STBY C-Mu, it was noted that the peptide was 30-60% more effective than STBY at inhibiting cell growth (FIGS. 18-20). In fact, automated cell-cell counting was inaccurate due to the increased amount of dead cells and debris (FIGS. 19-20). Forty micromolar C-Mu was as effective or more effective than 60 micromolar STBY. After the cells were stained with Trypan blue and manual counts obtained, it was determined that treatment with C-Mu STBY had resulted in a cell death of more than 90% in 10 hours of treatment (FIGS. 21-22).

Example 4

The structure of the Rpa43-Rrn3 complex established using x-ray crystallography will assist in the development of improved inhibitors of transcription based on the interaction between Rpa43 and Rrn3. For x-ray crystallography studies, recombinant FLAG-tagged-Rrn3 and GST-tagged 22mer are produced. The two proteins are then be combined and purified by sequential chromatography over anti-FLAG and GSH resins, followed by size exclusion chromatography (if necessary). This results in the purification of complexes of Rrn3 and GST-Rpa43 with equal stoichiometry and in quantities suitable for crystallization and X-ray crystallography. This information allows the modeling of the interaction, and is used to enhance the stability of the peptide-protein interaction in order to increase the efficacy of the peptide or the subsequent peptidomimetic compounds.

Example 5

Active mutated and/or truncated forms of the 22mer peptide are identified utilizing high-throughput screens of randomly mutagenized peptides using the same yeast two-hybrid screen used to establish the fact that Rpa43 and Rrn3 interact. In this case, an Rpa43 is constructed that contains restriction sites flanking the 22mer. The 22mer itself is amplified under conditions that cause the misincorporation of deoxynucleotides (random PCR mutagenesis), i.e. the substitution of manganese for magnesium and low concentrations of dGTP. The mutagenized 22mers are then ligated back into the vector that drives the expression of Rpa43 in yeast and used to transform yeast, which are used in two-hybrid analysis using a dosable selection system (e.g. Aureobasidin A) to select for forms of Rpa43 that bind better to Rrn3.

In a similar fashion, alanine-scanning mutagenesis is utilized instead of random mutagenesis to identify mutated/truncated forms of the 22 mer. Alanine-scanning mutagenesis is a simple and widely used technique in the determination of the catalytic or functional role of protein residues.

Example 6

Peptidomimetics are produced in accordance with the presently disclosed and claimed inventive concept(s). Said peptidomimetics are compounds which mimic the biological activity of the 22mer (or a fragment thereof) while offering the advantages of increased bioavailability, biostability, bioefficiency, and bioselectivity with regard to binding to cell permeability and binding to Rrn3, the biological target of the parent peptide. These can be either peptoids or D-peptides or non-peptide.

Thus, in accordance with the presently disclosed and claimed inventive concept(s), there have been provided compositions for inhibition of RNA polymerase I, as well as methods for producing and using same. Although the presently claimed and disclosed inventive concept(s) has been described in conjunction with the specific drawings and language set forth above, it is evident that many alternatives, modifications and variations will be apparent to those skilled in the art. Accordingly, it is intended to embrace all such alternatives, modifications and variations that fall within the spirit and broad scope of the inventive concept(s).

What is claimed is:

1. A method of inhibiting interaction of Rrn3 and Rpa43 in a cell, said method comprising at least one step selected from the group consisting of:
   (a) administering to said cell a composition comprising an isolated peptide fragment and an element attached thereto, the element comprising a tag containing a protein transduction domain attached to the N-terminus of the peptide fragment, wherein the protein transduction domain enables the composition to transduce across the membrane of the cell, wherein the composition enters a nucleolus of the cell and inhibits interaction of Rrn3 and Rpa43 within the nucleolus of the cell; and
   (b) introducing into a cell a recombinant vector comprising a nucleic acid sequence encoding a peptide fragment and an element attached thereto, the element comprising a tag containing a protein transduction domain attached to the N-terminus of the peptide fragment, wherein the peptide fragment is expressed within the cell and inhibits interaction of Rrn3 and Rpa43 within a nucleolus of the cell; and
   wherein each of the isolated peptide fragment of (a) and the peptide fragment encoded by the nucleic acid sequence of (b) is 22-27 amino acids in length and comprises the sequence of:
   (i) SEQ ID NO:1, SEQ ID NO:2, or SEQ ID NO:3;
   (ii) $X_1X_2X_3X_4X_5X_6H_7X_8G_9X_{10}L_{11}X_{12}H_{13}G_{14}X_{15}X_{16}N_{17}A_{18}S_{19}X_{20}P_{21}K_{22}$ (SEQ ID NO:4), wherein $X_1$ is N, F, or K; $X_2$ is K, R, L, or I; $X_3$ is V, Q, L, or M; $X_4$ is S, G, or A; $X_5$ is S, P, A, V, or T; $X_6$ is S or T; $X_8$ is I or V; $X_{10}$ is L or C; $X_{12}$ is V or I; $X_{15}$ is C, A, I, or T; $X_{16}$ is F or I; $X_{20}$ is I or V;
   (iii) amino acids 6-27 of SEQ ID NO:179;
   (iv) amino acids 4-25 of SEQ ID NO:180;
   (v) amino acids 4-25 of SEQ ID NO:181;
   (vi) amino acids 4-25 of SEQ ID NO:182;
   (vii) amino acids 4-25 of SEQ ID NO:183;
   (viii) amino acids 3-24 of SEQ ID NO:184;
   (ix) amino acids 3-24 of SEQ ID NO:185;
   (x) amino acids 4-25 of SEQ ID NO:186; or
   (xi) amino acids 5-26 of SEQ ID NO:187.

2. The method of claim 1, wherein the inhibition of interaction of Rrn3 and Rpa43 results in the inhibition of rDNA transcription.

3. The method of claim 1, wherein the inhibition of interaction of Rrn3 and Rpa43 results in the inhibition of synthesis of 45S pre-ribosomal RNA.

4. The method of claim 1, wherein the inhibition of interaction of Rrn3 and Rpa43 results in the inhibition of cell growth.

5. The method of claim 1, wherein the tag is a TAT peptide.

6. The method of claim 1, wherein the isolated peptide further comprises a fluorescent tag.

7. The method of claim 1, wherein the composition further comprises a targeting moiety.

8. A method of inhibiting interaction of Rrn3 and Rpa43 in a cell, the method comprising the step of:
   administering to said cell a composition comprising an isolated peptide fragment and an element attached thereto, the element comprising a tag containing a protein transduction domain attached to the N-terminus of the peptide fragment, wherein the protein transduction domain enables the composition to transduce across the membrane of the cell, and wherein the isolated peptide fragment is 22-27 amino acids in length and comprises the sequence of:
   (i) SEQ ID NO:1, SEQ ID NO:2, or SEQ ID NO:3;
   (ii) $X_1X_2X_3X_4X_5X_6H_7X_8G_9X_{10}L_{11}X_{12}H_{13}G_{14}X_{15}X_{16}N_{17}A_{18}S_{19}X_{20}P_{21}K_{22}$ (SEQ ID NO:4), wherein $X_1$ is N, F, or K; $X_2$ is K, R, L, or I; $X_3$ is V, Q, L, or M; $X_4$ is S, G, or A; $X_5$ is S, P, A, V, or T; $X_6$ is S or T; $X_8$ is I or V; $X_{10}$ is L or C; $X_{12}$ is V or I; $X_{15}$ is C, A, I, or T; $X_{16}$ is F or I; $X_{20}$ is I or V;
   (iii) amino acids 6-27 of SEQ ID NO:179;
   (iv) amino acids 4-25 of SEQ ID NO:180;
   (v) amino acids 4-25 of SEQ ID NO:181;
   (vi) amino acids 4-25 of SEQ ID NO:182;
   (vii) amino acids 4-25 of SEQ ID NO:183;
   (viii) amino acids 3-24 of SEQ ID NO:184;
   (ix) amino acids 3-24 of SEQ ID NO:185;
   (x) amino acids 4-25 of SEQ ID NO:186; or
   (xi) amino acids 5-26 of SEQ ID NO:187; and
   wherein the composition enters a nucleolus of the cell and inhibits interaction of Rrn3 and Rpa43 within the nucleolus of the cell.

9. The method of claim 8, wherein the inhibition of interaction of Rrn3 and Rpa43 results in the inhibition of rDNA transcription.

10. The method of claim 8, wherein the inhibition of interaction of Rrn3 and Rpa43 results in the inhibition of synthesis of 45S pre-ribosomal RNA.

11. The method of claim 8, wherein the inhibition of interaction of Rrn3 and Rpa43 results in the inhibition of cell growth.

12. A method of inhibiting interaction of Rrn3 and Rpa43 in a cell, the method comprising the steps of:
   (a) introducing into said cell a recombinant vector comprising a nucleic acid sequence encoding an isolated peptide fragment and an element attached thereto, the element comprising a tag containing a protein transduction domain attached to the N-terminus of the peptide fragment, wherein the isolated peptide fragment is 22-27 amino acids in length and comprises the sequence of:
   (i) SEQ ID NO:1, SEQ ID NO:2, or SEQ ID NO:3;
   (ii) $X_1X_2X_3X_4X_5X_6H_7X_8G_9X_{10}L_{11}X_{12}H_{13}G_{14}X_{15}X_{16}N_{17}A_{18}S_{19}X_{20}P_{21}K_{22}$ (SEQ ID NO:4), wherein $X_1$ is N, F, or K; $X_2$ is K, R, L, or I; $X_3$ is V, Q, L, or M; $X_4$ is S, G, or A; $X_5$ is S, P, A, V, or T; $X_6$ is S or T; $X_8$ is I or V; $X_{10}$ is L or C; $X_{12}$ is V or I; $X_{15}$ is C, A, I, or T; $X_{16}$ is F or I; $X_{20}$ is I or V;

(iii) amino acids 6-27 of SEQ ID NO:179;
(iv) amino acids 4-25 of SEQ ID NO:180;
(v) amino acids 4-25 of SEQ ID NO:181;
(vi) amino acids 4-25 of SEQ ID NO:182;
(vii) amino acids 4-25 of SEQ ID NO:183;
(viii) amino acids 3-24 of SEQ ID NO:184;
(ix) amino acids 3-24 of SEQ ID NO:185;
(x) amino acids 4-25 of SEQ ID NO:186; or
(xi) amino acids 5-26 of SEQ ID NO:187; and
(b) culturing the cell under conditions that allow for expression of the peptide fragment, wherein the peptide fragment is produced within the cell and inhibits interaction of Rrn3 and Rpa43 within the nucleolus of the cell.

13. The method of claim 12, wherein the inhibition of interaction of Rrn3 and Rpa43 results in the inhibition of rDNA transcription.

14. The method of claim 12, wherein the inhibition of interaction of Rrn3 and Rpa43 results in the inhibition of synthesis of 45S pre-ribosomal RNA.

15. The method of claim 12, wherein the inhibition of interaction of Rrn3 and Rpa43 results in the inhibition of cell growth.

16. The method of claim 1, wherein the inhibition of interaction of Rrn3 and Rpa43 results in cell death.

17. The method of claim 8, wherein the inhibition of interaction of Rrn3 and Rpa43 results in cell death.

18. The method of claim 8, wherein the isolated peptide further comprises a fluorescent tag.

19. The method of claim 12, wherein the inhibition of interaction of Rrn3 and Rpa43 results in cell death.

* * * * *

UNITED STATES PATENT AND TRADEMARK OFFICE
CERTIFICATE OF CORRECTION

PATENT NO. : 9,675,662 B2  
APPLICATION NO. : 13/309651  
DATED : June 13, 2017  
INVENTOR(S) : Lawrence Rothblum Page 1 of 1

It is certified that error appears in the above-identified patent and that said Letters Patent is hereby corrected as shown below:

In the Specification

Column 20, Line 66: Delete "MU" and replace with -- MTT --

Column 21, Line 17: Delete "DU." and replace with -- DTT. --

Column 22, Line 59: Delete "DU)" and replace with -- DTT) --

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 188

<210> SEQ ID NO 1
<211> LENGTH: 22
<212> TYPE: PRT
<213> ORGANISM: Homo sapiens

<400> SEQUENCE: 1

Asn Lys Val Ser Ser Ser His Ile Gly Cys Leu Val His Gly Cys Phe
1               5                   10                  15
```

```
Asn Ala Ser Ile Pro Lys
            20

<210> SEQ ID NO 2
<211> LENGTH: 22
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: any amino acid except Cys
<220> FEATURE:
<221> NAME/KEY: MISC_FEATURE
<222> LOCATION: (15)..(15)
<223> OTHER INFORMATION: any amino acid except Cys

<400> SEQUENCE: 2

Asn Lys Val Ser Ser Ser His Ile Gly Xaa Leu Val His Gly Xaa Phe
1               5                   10                  15

Asn Ala Ser Ile Pro Lys
            20

<210> SEQ ID NO 3
<211> LENGTH: 22
<212> TYPE: PRT
<213> ORGANISM: Homo sapiens

<400> SEQUENCE: 3

Asn Lys Val Ser Ser Ser His Ile Gly Ser Leu Val His Gly Ser Phe
1               5                   10                  15

Asn Ala Ser Ile Pro Lys
            20

<210> SEQ ID NO 4
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N, F or K
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: V, Q, L or M
<220> FEATURE:
<221> NAME/KEY: MISC_FEATURE
<222> LOCATION: (4)..(4)
<223> OTHER INFORMATION: S, G or A
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (8)..(8)
<223> OTHER INFORMATION: I or V
<220> FEATURE:
<221> NAME/KEY: MISC_FEATURE
<222> LOCATION: (10)..(10)
<223> OTHER INFORMATION: L or C
<220> FEATURE:
<221> NAME/KEY: MISC_FEATURE
```

```
<222> LOCATION: (12)..(12)
<223> OTHER INFORMATION: V or I
<220> FEATURE:
<221> NAME/KEY: MISC_FEATURE
<222> LOCATION: (15)..(15)
<223> OTHER INFORMATION: C, A, I, or T
<220> FEATURE:
<221> NAME/KEY: MISC_FEATURE
<222> LOCATION: (16)..(16)
<223> OTHER INFORMATION: F or I
<220> FEATURE:
<221> NAME/KEY: MISC_FEATURE
<222> LOCATION: (20)..(20)
<223> OTHER INFORMATION: I or V

<400> SEQUENCE: 4

Xaa Xaa Xaa Xaa Xaa Xaa His Xaa Gly Xaa Leu Xaa His Gly Xaa Xaa
1               5                   10                  15

Asn Ala Ser Xaa Pro Lys
            20

<210> SEQ ID NO 5
<211> LENGTH: 5
<212> TYPE: PRT
<213> ORGANISM: Homo sapiens

<400> SEQUENCE: 5

Asn Lys Val Ser Ser
1               5

<210> SEQ ID NO 6
<211> LENGTH: 5
<212> TYPE: PRT
<213> ORGANISM: Homo sapiens

<400> SEQUENCE: 6

Lys Val Ser Ser Ser
1               5

<210> SEQ ID NO 7
<211> LENGTH: 5
<212> TYPE: PRT
<213> ORGANISM: Homo sapiens

<400> SEQUENCE: 7

Val Ser Ser Ser His
1               5

<210> SEQ ID NO 8
<211> LENGTH: 5
<212> TYPE: PRT
<213> ORGANISM: Homo sapiens

<400> SEQUENCE: 8

Ser Ser Ser His Ile
1               5

<210> SEQ ID NO 9
<211> LENGTH: 5
<212> TYPE: PRT
<213> ORGANISM: Homo sapiens

<400> SEQUENCE: 9

Ser Ser His Ile Gly
1               5
```

```
<210> SEQ ID NO 10
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 10

Ser His Ile Gly Xaa
1               5

<210> SEQ ID NO 11
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

His Ile Gly Xaa Leu
1               5

<210> SEQ ID NO 12
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Ile Gly Xaa Leu Val
1               5

<210> SEQ ID NO 13
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 13

Gly Xaa Leu Val His
1               5

<210> SEQ ID NO 14
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Leu Val His Gly
1               5

<210> SEQ ID NO 15
<211> LENGTH: 5
<212> TYPE: PRT
<213> ORGANISM: Homo sapiens
```

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Leu Val His Gly Xaa
1               5

<210> SEQ ID NO 16
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Val His Gly Xaa Phe
1               5

<210> SEQ ID NO 17
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

His Gly Xaa Phe Asn
1               5

<210> SEQ ID NO 18
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 18

Gly Xaa Phe Asn Ala
1               5

<210> SEQ ID NO 19
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 19

Xaa Phe Asn Ala Ser
1               5

<210> SEQ ID NO 20
<211> LENGTH: 5
<212> TYPE: PRT
<213> ORGANISM: Homo sapiens

<400> SEQUENCE: 20

Phe Asn Ala Ser Ile
```

1               5

<210> SEQ ID NO 21
<211> LENGTH: 5
<212> TYPE: PRT
<213> ORGANISM: Homo sapiens

<400> SEQUENCE: 21

Asn Ala Ser Ile Pro
1               5

<210> SEQ ID NO 22
<211> LENGTH: 5
<212> TYPE: PRT
<213> ORGANISM: Homo sapiens

<400> SEQUENCE: 22

Ala Ser Ile Pro Lys
1               5

<210> SEQ ID NO 23
<211> LENGTH: 6
<212> TYPE: PRT
<213> ORGANISM: Homo sapiens

<400> SEQUENCE: 23

Asn Lys Val Ser Ser Ser
1               5

<210> SEQ ID NO 24
<211> LENGTH: 6
<212> TYPE: PRT
<213> ORGANISM: Homo sapiens

<400> SEQUENCE: 24

Lys Val Ser Ser Ser His
1               5

<210> SEQ ID NO 25
<211> LENGTH: 6
<212> TYPE: PRT
<213> ORGANISM: Homo sapiens

<400> SEQUENCE: 25

Val Ser Ser Ser His Ile
1               5

<210> SEQ ID NO 26
<211> LENGTH: 6
<212> TYPE: PRT
<213> ORGANISM: Homo sapiens

<400> SEQUENCE: 26

Ser Ser Ser His Ile Gly
1               5

<210> SEQ ID NO 27
<211> LENGTH: 6
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 27

```
Ser Ser His Ile Gly Xaa
1               5

<210> SEQ ID NO 28
<211> LENGTH: 6
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 28

Ser His Ile Gly Xaa Leu
1               5

<210> SEQ ID NO 29
<211> LENGTH: 6
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 29

His Ile Gly Xaa Leu Val
1               5

<210> SEQ ID NO 30
<211> LENGTH: 6
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 30

Ile Gly Xaa Leu Val His
1               5

<210> SEQ ID NO 31
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 31

Gly Xaa Leu Val His Gly
1               5

<210> SEQ ID NO 32
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 32
```

Xaa Leu Val His Gly Xaa
1               5

<210> SEQ ID NO 33
<211> LENGTH: 6
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Leu Val His Gly Xaa Phe
1               5

<210> SEQ ID NO 34
<211> LENGTH: 6
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Val His Gly Xaa Phe Asn
1               5

<210> SEQ ID NO 35
<211> LENGTH: 6
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 35

His Gly Xaa Phe Asn Ala
1               5

<210> SEQ ID NO 36
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 36

Gly Xaa Phe Asn Ala Ser
1               5

<210> SEQ ID NO 37
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 37

Xaa Phe Asn Ala Ser Ile
1               5

<210> SEQ ID NO 38
<211> LENGTH: 6
<212> TYPE: PRT
<213> ORGANISM: Homo sapiens

<400> SEQUENCE: 38

Phe Asn Ala Ser Ile Pro
1               5

<210> SEQ ID NO 39
<211> LENGTH: 6
<212> TYPE: PRT
<213> ORGANISM: Homo sapiens

<400> SEQUENCE: 39

Asn Ala Ser Ile Pro Lys
1               5

<210> SEQ ID NO 40
<211> LENGTH: 7
<212> TYPE: PRT
<213> ORGANISM: Homo sapiens

<400> SEQUENCE: 40

Asn Lys Val Ser Ser Ser His
1               5

<210> SEQ ID NO 41
<211> LENGTH: 7
<212> TYPE: PRT
<213> ORGANISM: Homo sapiens

<400> SEQUENCE: 41

Lys Val Ser Ser Ser His Ile
1               5

<210> SEQ ID NO 42
<211> LENGTH: 7
<212> TYPE: PRT
<213> ORGANISM: Homo sapiens

<400> SEQUENCE: 42

Val Ser Ser Ser His Ile Gly
1               5

<210> SEQ ID NO 43
<211> LENGTH: 7
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 43

Ser Ser Ser His Ile Gly Xaa
1               5

<210> SEQ ID NO 44
<211> LENGTH: 7
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

```
<400> SEQUENCE: 44

Ser Ser His Ile Gly Xaa Leu
1               5

<210> SEQ ID NO 45
<211> LENGTH: 7
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 45

Ser His Ile Gly Xaa Leu Val
1               5

<210> SEQ ID NO 46
<211> LENGTH: 7
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

His Ile Gly Xaa Leu Val His
1               5

<210> SEQ ID NO 47
<211> LENGTH: 7
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 47

Ile Gly Xaa Leu Val His Gly
1               5

<210> SEQ ID NO 48
<211> LENGTH: 7
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 48

Gly Xaa Leu Val His Gly Xaa
1               5

<210> SEQ ID NO 49
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
```

<220> FEATURE:
<221> NAME/KEY: misc_feature
<222> LOCATION: (6)..(6)
<223> OTHER INFORMATION: Xaa can be any naturally occurring amino acid

<400> SEQUENCE: 49

Xaa Leu Val His Gly Xaa Phe
1               5

<210> SEQ ID NO 50
<211> LENGTH: 7
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 50

Leu Val His Gly Xaa Phe Asn
1               5

<210> SEQ ID NO 51
<211> LENGTH: 7
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 51

Val His Gly Xaa Phe Asn Ala
1               5

<210> SEQ ID NO 52
<211> LENGTH: 7
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 52

His Gly Xaa Phe Asn Ala Ser
1               5

<210> SEQ ID NO 53
<211> LENGTH: 7
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 53

Gly Xaa Phe Asn Ala Ser Ile
1               5

<210> SEQ ID NO 54
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

```
<400> SEQUENCE: 54

Xaa Phe Asn Ala Ser Ile Pro
1               5

<210> SEQ ID NO 55
<211> LENGTH: 7
<212> TYPE: PRT
<213> ORGANISM: Homo sapiens

<400> SEQUENCE: 55

Phe Asn Ala Ser Ile Pro Lys
1               5

<210> SEQ ID NO 56
<211> LENGTH: 8
<212> TYPE: PRT
<213> ORGANISM: Homo sapiens

<400> SEQUENCE: 56

Asn Lys Val Ser Ser Ser His Ile
1               5

<210> SEQ ID NO 57
<211> LENGTH: 8
<212> TYPE: PRT
<213> ORGANISM: Homo sapiens

<400> SEQUENCE: 57

Lys Val Ser Ser Ser His Ile Gly
1               5

<210> SEQ ID NO 58
<211> LENGTH: 8
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 58

Val Ser Ser Ser His Ile Gly Xaa
1               5

<210> SEQ ID NO 59
<211> LENGTH: 8
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 59

Ser Ser Ser His Ile Gly Xaa Leu
1               5

<210> SEQ ID NO 60
<211> LENGTH: 8
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 60

Ser Ser His Ile Gly Xaa Leu Val
1               5

<210> SEQ ID NO 61
<211> LENGTH: 8
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 61

Ser His Ile Gly Xaa Leu Val His
1               5

<210> SEQ ID NO 62
<211> LENGTH: 8
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 62

His Ile Gly Xaa Leu Val His Gly
1               5

<210> SEQ ID NO 63
<211> LENGTH: 8
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 63

Ile Gly Xaa Leu Val His Gly Xaa
1               5

<210> SEQ ID NO 64
<211> LENGTH: 8
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 64

Gly Xaa Leu Val His Gly Xaa Phe
1               5

<210> SEQ ID NO 65
<211> LENGTH: 8
<212> TYPE: PRT
<213> ORGANISM: Homo sapiens
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 65

Xaa Leu Val His Gly Xaa Phe Asn
1               5

<210> SEQ ID NO 66
<211> LENGTH: 8
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 66

Leu Val His Gly Xaa Phe Asn Ala
1               5

<210> SEQ ID NO 67
<211> LENGTH: 8
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 67

Val His Gly Xaa Phe Asn Ala Ser
1               5

<210> SEQ ID NO 68
<211> LENGTH: 8
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 68

His Gly Xaa Phe Asn Ala Ser Ile
1               5

<210> SEQ ID NO 69
<211> LENGTH: 8
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 69

Gly Xaa Phe Asn Ala Ser Ile Pro
1               5

<210> SEQ ID NO 70
<211> LENGTH: 8
<212> TYPE: PRT
<213> ORGANISM: Homo sapiens
<220> FEATURE:
```

```
<221> NAME/KEY: misc_feature
<222> LOCATION: (1)..(1)
<223> OTHER INFORMATION: Xaa can be any naturally occurring amino acid

<400> SEQUENCE: 70

Xaa Phe Asn Ala Ser Ile Pro Lys
1               5

<210> SEQ ID NO 71
<211> LENGTH: 9
<212> TYPE: PRT
<213> ORGANISM: Homo sapiens

<400> SEQUENCE: 71

Asn Lys Val Ser Ser Ser His Ile Gly
1               5

<210> SEQ ID NO 72
<211> LENGTH: 9
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 72

Lys Val Ser Ser Ser His Ile Gly Xaa
1               5

<210> SEQ ID NO 73
<211> LENGTH: 9
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 73

Val Ser Ser Ser His Ile Gly Xaa Leu
1               5

<210> SEQ ID NO 74
<211> LENGTH: 9
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 74

Ser Ser Ser His Ile Gly Xaa Leu Val
1               5

<210> SEQ ID NO 75
<211> LENGTH: 9
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 75

Ser Ser His Ile Gly Xaa Leu Val His
1               5
```

```
<210> SEQ ID NO 76
<211> LENGTH: 9
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 76

Ser His Ile Gly Xaa Leu Val His Gly
 1               5

<210> SEQ ID NO 77
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 77

His Ile Gly Xaa Leu Val His Gly Xaa
 1               5

<210> SEQ ID NO 78
<211> LENGTH: 9
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 78

Ile Gly Xaa Leu Val His Gly Xaa Phe
 1               5

<210> SEQ ID NO 79
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 79

Gly Xaa Leu Val His Gly Xaa Phe Asn
 1               5

<210> SEQ ID NO 80
<211> LENGTH: 9
<212> TYPE: PRT
<213> ORGANISM: Homo sapiens
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 80

Xaa Leu Val His Gly Xaa Phe Asn Ala
1               5

<210> SEQ ID NO 81
<211> LENGTH: 9
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 81

Leu Val His Gly Xaa Phe Asn Ala Ser
1               5

<210> SEQ ID NO 82
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 82

Val His Gly Xaa Phe Asn Ala Ser Ile
1               5

<210> SEQ ID NO 83
<211> LENGTH: 9
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 83

His Gly Xaa Phe Asn Ala Ser Ile Pro
1               5

<210> SEQ ID NO 84
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 84

Gly Xaa Phe Asn Ala Ser Ile Pro Lys
1               5

<210> SEQ ID NO 85
<211> LENGTH: 10
<212> TYPE: PRT
<213> ORGANISM: Homo sapiens
<220> FEATURE:
```

<220> FEATURE:
<221> NAME/KEY: misc_feature
<222> LOCATION: (10)..(10)
<223> OTHER INFORMATION: Xaa can be any naturally occurring amino acid

<400> SEQUENCE: 85

Asn Lys Val Ser Ser Ser His Ile Gly Xaa
1               5                   10

<210> SEQ ID NO 86
<211> LENGTH: 10
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 86

Lys Val Ser Ser Ser His Ile Gly Xaa Leu
1               5                   10

<210> SEQ ID NO 87
<211> LENGTH: 10
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 87

Val Ser Ser Ser His Ile Gly Xaa Leu Val
1               5                   10

<210> SEQ ID NO 88
<211> LENGTH: 10
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 88

Ser Ser Ser His Ile Gly Xaa Leu Val His
1               5                   10

<210> SEQ ID NO 89
<211> LENGTH: 10
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Ser Ser His Ile Gly Xaa Leu Val His Gly
1               5                   10

<210> SEQ ID NO 90
<211> LENGTH: 10
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:

```
<221> NAME/KEY: misc_feature
<222> LOCATION: (10)..(10)
<223> OTHER INFORMATION: Xaa can be any naturally occurring amino acid

<400> SEQUENCE: 90

Ser His Ile Gly Xaa Leu Val His Gly Xaa
1               5                   10

<210> SEQ ID NO 91
<211> LENGTH: 10
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 91

His Ile Gly Xaa Leu Val His Gly Xaa Phe
1               5                   10

<210> SEQ ID NO 92
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 92

Ile Gly Xaa Leu Val His Gly Xaa Phe Asn
1               5                   10

<210> SEQ ID NO 93
<211> LENGTH: 10
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 93

Gly Xaa Leu Val His Gly Xaa Phe Asn Ala
1               5                   10

<210> SEQ ID NO 94
<211> LENGTH: 10
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

<400> SEQUENCE: 94

Xaa Leu Val His Gly Xaa Phe Asn Ala Ser
1               5                   10

<210> SEQ ID NO 95
<211> LENGTH: 10
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 95

Leu Val His Gly Xaa Phe Asn Ala Ser Ile
1               5                   10

<210> SEQ ID NO 96
<211> LENGTH: 10
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 96

Val His Gly Xaa Phe Asn Ala Ser Ile Pro
1               5                   10

<210> SEQ ID NO 97
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 97

His Gly Xaa Phe Asn Ala Ser Ile Pro Lys
1               5                   10

<210> SEQ ID NO 98
<211> LENGTH: 11
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 98

Asn Lys Val Ser Ser Ser His Ile Gly Xaa Leu
1               5                   10

<210> SEQ ID NO 99
<211> LENGTH: 11
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 99

Lys Val Ser Ser Ser His Ile Gly Xaa Leu Val

```
<210> SEQ ID NO 100
<211> LENGTH: 11
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 100

Val Ser Ser Ser His Ile Gly Xaa Leu Val His
1               5                   10

<210> SEQ ID NO 101
<211> LENGTH: 11
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 101

Ser Ser Ser His Ile Gly Xaa Leu Val His Gly
1               5                   10

<210> SEQ ID NO 102
<211> LENGTH: 11
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 102

Ser Ser His Ile Gly Xaa Leu Val His Gly Xaa
1               5                   10

<210> SEQ ID NO 103
<211> LENGTH: 11
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 103

Ser His Ile Gly Xaa Leu Val His Gly Xaa Phe
1               5                   10

<210> SEQ ID NO 104
<211> LENGTH: 11
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
```

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 104

His Ile Gly Xaa Leu Val His Gly Xaa Phe Asn
1               5                   10

<210> SEQ ID NO 105
<211> LENGTH: 11
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 105

Ile Gly Xaa Leu Val His Gly Xaa Phe Asn Ala
1               5                   10

<210> SEQ ID NO 106
<211> LENGTH: 11
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 106

Gly Xaa Leu Val His Gly Xaa Phe Asn Ala Ser
1               5                   10

<210> SEQ ID NO 107
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 107

Xaa Leu Val His Gly Xaa Phe Asn Ala Ser Ile
1               5                   10

<210> SEQ ID NO 108
<211> LENGTH: 11
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 108
```

```
Leu Val His Gly Xaa Phe Asn Ala Ser Ile Pro
1               5                   10
```

<210> SEQ ID NO 109
<211> LENGTH: 11
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 109

```
Val His Gly Xaa Phe Asn Ala Ser Ile Pro Lys
1               5                   10
```

<210> SEQ ID NO 110
<211> LENGTH: 12
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 110

```
Asn Lys Val Ser Ser Ser His Ile Gly Xaa Leu Val
1               5                   10
```

<210> SEQ ID NO 111
<211> LENGTH: 12
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 111

```
Lys Val Ser Ser Ser His Ile Gly Xaa Leu Val His
1               5                   10
```

<210> SEQ ID NO 112
<211> LENGTH: 12
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 112

```
Val Ser Ser Ser His Ile Gly Xaa Leu Val His Gly
1               5                   10
```

<210> SEQ ID NO 113
<211> LENGTH: 12
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 113

-continued

Ser Ser Ser His Ile Gly Xaa Leu Val His Gly Xaa
1               5                   10

<210> SEQ ID NO 114
<211> LENGTH: 12
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 114

Ser Ser His Ile Gly Xaa Leu Val His Gly Xaa Phe
1               5                   10

<210> SEQ ID NO 115
<211> LENGTH: 12
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 115

Ser His Ile Gly Xaa Leu Val His Gly Xaa Phe Asn
1               5                   10

<210> SEQ ID NO 116
<211> LENGTH: 12
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 116

His Ile Gly Xaa Leu Val His Gly Xaa Phe Asn Ala
1               5                   10

<210> SEQ ID NO 117
<211> LENGTH: 12
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 117

Ile Gly Xaa Leu Val His Gly Xaa Phe Asn Ala Ser
1               5                   10

```
<210> SEQ ID NO 118
<211> LENGTH: 12
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 118

Gly Xaa Leu Val His Gly Xaa Phe Asn Ala Ser Ile
1               5                   10

<210> SEQ ID NO 119
<211> LENGTH: 12
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 119

Xaa Leu Val His Gly Xaa Phe Asn Ala Ser Ile Pro
1               5                   10

<210> SEQ ID NO 120
<211> LENGTH: 12
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 120

Leu Val His Gly Xaa Phe Asn Ala Ser Ile Pro Lys
1               5                   10

<210> SEQ ID NO 121
<211> LENGTH: 13
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 121

Asn Lys Val Ser Ser Ser His Ile Gly Xaa Leu Val His
1               5                   10

<210> SEQ ID NO 122
<211> LENGTH: 13
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 122
```

```
Lys Val Ser Ser His Ile Gly Xaa Leu Val His Gly
1               5                   10
```

<210> SEQ ID NO 123
<211> LENGTH: 13
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 123

```
Val Ser Ser His Ile Gly Xaa Leu Val His Gly Xaa
1               5                   10
```

<210> SEQ ID NO 124
<211> LENGTH: 13
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 124

```
Ser Ser His Ile Gly Xaa Leu Val His Gly Xaa Phe
1               5                   10
```

<210> SEQ ID NO 125
<211> LENGTH: 13
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 125

```
Ser His Ile Gly Xaa Leu Val His Gly Xaa Phe Asn
1               5                   10
```

<210> SEQ ID NO 126
<211> LENGTH: 13
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 126

```
Ser His Ile Gly Xaa Leu Val His Gly Xaa Phe Asn Ala
1               5                   10
```

<210> SEQ ID NO 127
<211> LENGTH: 13
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 127

His Ile Gly Xaa Leu Val His Gly Xaa Phe Asn Ala Ser
1               5                   10

<210> SEQ ID NO 128
<211> LENGTH: 13
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 128

Ile Gly Xaa Leu Val His Gly Xaa Phe Asn Ala Ser Ile
1               5                   10

<210> SEQ ID NO 129
<211> LENGTH: 13
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 129

Gly Xaa Leu Val His Gly Xaa Phe Asn Ala Ser Ile Pro
1               5                   10

<210> SEQ ID NO 130
<211> LENGTH: 13
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 130

Xaa Leu Val His Gly Xaa Phe Asn Ala Ser Ile Pro Lys
1               5                   10

<210> SEQ ID NO 131

```
<211> LENGTH: 14
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 131

Asn Lys Val Ser Ser Ser His Ile Gly Xaa Leu Val His Gly
1               5                   10

<210> SEQ ID NO 132
<211> LENGTH: 14
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 132

Lys Val Ser Ser Ser His Ile Gly Xaa Leu Val His Gly Xaa
1               5                   10

<210> SEQ ID NO 133
<211> LENGTH: 14
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 133

Val Ser Ser Ser His Ile Gly Xaa Leu Val His Gly Xaa Phe
1               5                   10

<210> SEQ ID NO 134
<211> LENGTH: 14
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 134

Ser Ser Ser His Ile Gly Xaa Leu Val His Gly Xaa Phe Asn
1               5                   10

<210> SEQ ID NO 135
<211> LENGTH: 14
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
```

<220> FEATURE:
<221> NAME/KEY: misc_feature
<222> LOCATION: (11)..(11)
<223> OTHER INFORMATION: Xaa can be any naturally occurring amino acid

<400> SEQUENCE: 135

Ser Ser His Ile Gly Xaa Leu Val His Gly Xaa Phe Asn Ala
1               5                   10

<210> SEQ ID NO 136
<211> LENGTH: 14
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 136

Ser His Ile Gly Xaa Leu Val His Gly Xaa Phe Asn Ala Ser
1               5                   10

<210> SEQ ID NO 137
<211> LENGTH: 14
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 137

His Ile Gly Xaa Leu Val His Gly Xaa Phe Asn Ala Ser Ile
1               5                   10

<210> SEQ ID NO 138
<211> LENGTH: 14
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 138

Ile Gly Xaa Leu Val His Gly Xaa Phe Asn Ala Ser Ile Pro
1               5                   10

<210> SEQ ID NO 139
<211> LENGTH: 14
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)

```
<223> OTHER INFORMATION: Xaa can be any naturally occurring amino acid

<400> SEQUENCE: 139

Gly Xaa Leu Val His Gly Xaa Phe Asn Ala Ser Ile Pro Lys
1               5                   10

<210> SEQ ID NO 140
<211> LENGTH: 15
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 140

Asn Lys Val Ser Ser Ser His Ile Gly Xaa Leu Val His Gly Xaa
1               5                   10                  15

<210> SEQ ID NO 141
<211> LENGTH: 15
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 141

Lys Val Ser Ser Ser His Ile Gly Xaa Leu Val His Gly Xaa Phe
1               5                   10                  15

<210> SEQ ID NO 142
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 142

Val Ser Ser Ser His Ile Gly Xaa Leu Val His Gly Xaa Phe Asn
1               5                   10                  15

<210> SEQ ID NO 143
<211> LENGTH: 15
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 143
```

```
Ser Ser Ser His Ile Gly Xaa Leu Val His Gly Xaa Phe Asn Ala
1               5                   10                  15

<210> SEQ ID NO 144
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 144

Ser Ser His Ile Gly Xaa Leu Val His Gly Xaa Phe Asn Ala Ser
1               5                   10                  15

<210> SEQ ID NO 145
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 145

Ser His Ile Gly Xaa Leu Val His Gly Xaa Phe Asn Ala Ser Ile
1               5                   10                  15

<210> SEQ ID NO 146
<211> LENGTH: 15
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 146

His Ile Gly Xaa Leu Val His Gly Xaa Phe Asn Ala Ser Ile Pro
1               5                   10                  15

<210> SEQ ID NO 147
<211> LENGTH: 15
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 147

Ile Gly Xaa Leu Val His Gly Xaa Phe Asn Ala Ser Ile Pro Lys
1               5                   10                  15
```

<210> SEQ ID NO 148
<211> LENGTH: 16
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 148

Asn Lys Val Ser Ser Ser His Ile Gly Xaa Leu Val His Gly Xaa Phe
1               5                   10                  15

<210> SEQ ID NO 149
<211> LENGTH: 16
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 149

Lys Val Ser Ser Ser His Ile Gly Xaa Leu Val His Gly Xaa Phe Asn
1               5                   10                  15

<210> SEQ ID NO 150
<211> LENGTH: 16
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 150

Val Ser Ser Ser His Ile Gly Xaa Leu Val His Gly Xaa Phe Asn Ala
1               5                   10                  15

<210> SEQ ID NO 151
<211> LENGTH: 16
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 151

Ser Ser Ser His Ile Gly Xaa Leu Val His Gly Xaa Phe Asn Ala Ser
1               5                   10                  15

<210> SEQ ID NO 152

```
<211> LENGTH: 16
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 152

Ser Ser His Ile Gly Xaa Leu Val His Gly Xaa Phe Asn Ala Ser Ile
1               5                   10                  15

<210> SEQ ID NO 153
<211> LENGTH: 16
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 153

Ser His Ile Gly Xaa Leu Val His Gly Xaa Phe Asn Ala Ser Ile Pro
1               5                   10                  15

<210> SEQ ID NO 154
<211> LENGTH: 16
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 154

His Ile Gly Xaa Leu Val His Gly Xaa Phe Asn Ala Ser Ile Pro Lys
1               5                   10                  15

<210> SEQ ID NO 155
<211> LENGTH: 17
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 155

Asn Lys Val Ser Ser Ser His Ile Gly Xaa Leu Val His Gly Xaa Phe
1               5                   10                  15

Asn

<210> SEQ ID NO 156
<211> LENGTH: 17
```

```
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 156

Lys Val Ser Ser Ser His Ile Gly Xaa Leu Val His Gly Xaa Phe Asn
1               5                   10                  15

Ala

<210> SEQ ID NO 157
<211> LENGTH: 17
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 157

Val Ser Ser Ser His Ile Gly Xaa Leu Val His Gly Xaa Phe Asn Ala
1               5                   10                  15

Ser

<210> SEQ ID NO 158
<211> LENGTH: 17
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 158

Ser Ser Ser His Ile Gly Xaa Leu Val His Gly Xaa Phe Asn Ala Ser
1               5                   10                  15

Ile

<210> SEQ ID NO 159
<211> LENGTH: 17
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 159

Ser Ser His Ile Gly Xaa Leu Val His Gly Xaa Phe Asn Ala Ser Ile
1               5                   10                  15
```

Pro

<210> SEQ ID NO 160
<211> LENGTH: 17
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 160

Ser His Ile Gly Xaa Leu Val His Gly Xaa Phe Asn Ala Ser Ile Pro
1               5                   10                  15

Lys

<210> SEQ ID NO 161
<211> LENGTH: 18
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 161

Asn Lys Val Ser Ser Ser His Ile Gly Xaa Leu Val His Gly Xaa Phe
1               5                   10                  15

Asn Ala

<210> SEQ ID NO 162
<211> LENGTH: 18
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 162

Lys Val Ser Ser Ser His Ile Gly Xaa Leu Val His Gly Xaa Phe Asn
1               5                   10                  15

Ala Ser

<210> SEQ ID NO 163
<211> LENGTH: 18
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid -continued

<400> SEQUENCE: 163

Val Ser Ser Ser His Ile Gly Xaa Leu Val His Gly Xaa Phe Asn Ala
1               5                   10                  15

Ser Ile

<210> SEQ ID NO 164
<211> LENGTH: 18
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 164

Ser Ser Ser His Ile Gly Xaa Leu Val His Gly Xaa Phe Asn Ala Ser
1               5                   10                  15

Ile Pro

<210> SEQ ID NO 165
<211> LENGTH: 18
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 165

Ser Ser His Ile Gly Xaa Leu Val His Gly Xaa Phe Asn Ala Ser Ile
1               5                   10                  15

Pro Lys

<210> SEQ ID NO 166
<211> LENGTH: 19
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 166

Asn Lys Val Ser Ser Ser His Ile Gly Xaa Leu Val His Gly Xaa Phe
1               5                   10                  15

Asn Ala Ser

<210> SEQ ID NO 167
<211> LENGTH: 19
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

```
<220> FEATURE:
<221> NAME/KEY: misc_feature
<222> LOCATION: (14)..(14)
<223> OTHER INFORMATION: Xaa can be any naturally occurring amino acid

<400> SEQUENCE: 167

Lys Val Ser Ser Ser His Ile Gly Xaa Leu Val His Gly Xaa Phe Asn
1               5                   10                  15

Ala Ser Ile

<210> SEQ ID NO 168
<211> LENGTH: 19
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 168

Val Ser Ser Ser His Ile Gly Xaa Leu Val His Gly Xaa Phe Asn Ala
1               5                   10                  15

Ser Ile Pro

<210> SEQ ID NO 169
<211> LENGTH: 19
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 169

Ser Ser Ser His Ile Gly Xaa Leu Val His Gly Xaa Phe Asn Ala Ser
1               5                   10                  15

Ile Pro Lys

<210> SEQ ID NO 170
<211> LENGTH: 20
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 170

Asn Lys Val Ser Ser Ser His Ile Gly Xaa Leu Val His Gly Xaa Phe
1               5                   10                  15

Asn Ala Ser Ile
            20

<210> SEQ ID NO 171
<211> LENGTH: 20
```

```
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 171

Lys Val Ser Ser Ser His Ile Gly Xaa Leu Val His Gly Xaa Phe Asn
1               5                   10                  15

Ala Ser Ile Pro
            20

<210> SEQ ID NO 172
<211> LENGTH: 20
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 172

Val Ser Ser Ser His Ile Gly Xaa Leu Val His Gly Xaa Phe Asn Ala
1               5                   10                  15

Ser Ile Pro Lys
            20

<210> SEQ ID NO 173
<211> LENGTH: 21
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 173

Asn Lys Val Ser Ser Ser His Ile Gly Xaa Leu Val His Gly Xaa Phe
1               5                   10                  15

Asn Ala Ser Ile Pro
                20

<210> SEQ ID NO 174
<211> LENGTH: 21
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 174
```

-continued

Lys Val Ser Ser Ser His Ile Gly Xaa Leu Val His Gly Xaa Phe Asn
1               5                   10                  15

Ala Ser Ile Pro Lys
            20

<210> SEQ ID NO 175
<211> LENGTH: 32
<212> TYPE: PRT
<213> ORGANISM: Artificial Sequence
<220> FEATURE:
<223> OTHER INFORMATION: 1st ten amino acids are TAT peptide from HIV;
      last 22 amino acids are from Homo sapiens

<400> SEQUENCE: 175

Tyr Gly Arg Lys Lys Glu Glu Gln Arg Arg Asn Lys Val Ser Ser
1               5                   10                  15

His Ile Gly Cys Leu Val His Gly Cys Phe Asn Ala Ser Ile Pro Lys
                20                  25                  30

<210> SEQ ID NO 176
<211> LENGTH: 10
<212> TYPE: PRT
<213> ORGANISM: Human immunodeficiency virus

<400> SEQUENCE: 176

Tyr Gly Arg Lys Lys Glu Glu Gln Arg Arg
1               5                   10

<210> SEQ ID NO 177
<211> LENGTH: 22
<212> TYPE: PRT
<213> ORGANISM: Homo sapiens

<400> SEQUENCE: 177

Asn Lys Val Ser Ser His Ile Gly Cys Leu Val His Gly Cys Phe
1               5                   10                  15

Asn Ala Ser Ile Pro Lys
            20

<210> SEQ ID NO 178
<211> LENGTH: 30
<212> TYPE: PRT
<213> ORGANISM: Homo sapiens

<400> SEQUENCE: 178

Leu Met Gly Ile Val Asn Lys Val Ser Ser His Ile Gly Cys Leu
1               5                   10                  15

Val His Gly Cys Phe Asn Ala Ser Ile Pro Lys Pro Glu Gln
                20                  25                  30

<210> SEQ ID NO 179
<211> LENGTH: 30
<212> TYPE: PRT
<213> ORGANISM: Mus musculus

<400> SEQUENCE: 179

Leu Met Gly Thr Val Asn Lys Val Ser Ser His Ile Gly Cys Leu
1               5                   10                  15

Val His Gly Cys Phe Asn Ala Ser Ile Pro Lys Pro Glu Gln
                20                  25                  30

<210> SEQ ID NO 180
<211> LENGTH: 25

```
<212> TYPE: PRT
<213> ORGANISM: Bos taurus

<400> SEQUENCE: 180

Gly Thr Val Asn Lys Val Ser Ser His Ile Gly Cys Leu Val His
1               5                   10                  15

Gly Cys Phe Asn Ala Ser Ile Pro Lys
            20                  25

<210> SEQ ID NO 181
<211> LENGTH: 25
<212> TYPE: PRT
<213> ORGANISM: Equus caballus

<400> SEQUENCE: 181

Gly Thr Val Asn Lys Val Ser Ser His Ile Gly Cys Leu Val His
1               5                   10                  15

Gly Cys Phe Asn Ala Ser Ile Pro Lys
            20                  25

<210> SEQ ID NO 182
<211> LENGTH: 25
<212> TYPE: PRT
<213> ORGANISM: Xenopus laevis

<400> SEQUENCE: 182

Gly Ile Val Asn Lys Val Ala Pro Thr His Ile Gly Cys Leu Val His
1               5                   10                  15

Gly Cys Phe Asn Ala Ser Ile Pro Lys
            20                  25

<210> SEQ ID NO 183
<211> LENGTH: 29
<212> TYPE: PRT
<213> ORGANISM: Danio rerio

<400> SEQUENCE: 183

Gly Val Ile Asn Lys Met Gly Ala Ser His Val Gly Cys Leu Val His
1               5                   10                  15

Gly Cys Phe Asn Ala Ser Val Met Lys Pro Asn Ala Leu
            20                  25

<210> SEQ ID NO 184
<211> LENGTH: 29
<212> TYPE: PRT
<213> ORGANISM: Salmo salar

<400> SEQUENCE: 184

Thr Val Asn Lys Leu Gly Val Ser His Val Gly Cys Leu Val His Gly
1               5                   10                  15

Cys Phe Asn Ala Ser Val Pro Lys Pro Ala His Val Thr
            20                  25

<210> SEQ ID NO 185
<211> LENGTH: 28
<212> TYPE: PRT
<213> ORGANISM: Dictyostelium discoideum

<400> SEQUENCE: 185

Val Val Lys Arg Val Ser Thr Thr His Ile Ser Leu Leu Val Phe Gly
1               5                   10                  15

Thr Ile Ser Ala Ser Ile Pro Lys Ser Asn Ile Pro
```

```
                        20                  25

<210> SEQ ID NO 186
<211> LENGTH: 40
<212> TYPE: PRT
<213> ORGANISM: Schizosaccharomyces pombe

<400> SEQUENCE: 186

Gly Lys Ile Asn Leu Val Ser Pro Ser His Ile Gly Leu Leu Ile Leu
1               5                   10                  15

Gly Ile Phe Asn Ala Ser Ile Pro Arg Lys Ser Ile Pro Lys Asp Trp
            20                  25                  30

Ile Phe Ile Glu Pro Asp Thr Thr
        35                  40

<210> SEQ ID NO 187
<211> LENGTH: 37
<212> TYPE: PRT
<213> ORGANISM: Saccharomyces cerevisiae

<400> SEQUENCE: 187

Leu Gly Tyr Ile Phe Ile Gln Ser Ala Ser His Ile Gly Leu Leu Ile
1               5                   10                  15

His Asp Ala Phe Asn Ala Ser Ile Lys Lys Asn Asn Ile Pro Val Asp
            20                  25                  30

Trp Thr Phe Val His
        35

<210> SEQ ID NO 188
<211> LENGTH: 25
<212> TYPE: PRT
<213> ORGANISM: Artificial sequence
<220> FEATURE:
<223> OTHER INFORMATION: Consensus sequence of SEQ ID NOS:177-187
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: S or T
<220> FEATURE:
<221> NAME/KEY: MISC_FEATURE
<222> LOCATION: (11)..(11)
<223> OTHER INFORMATION: I or V
<220> FEATURE:
<221> NAME/KEY: MISC_FEATURE
<222> LOCATION: (13)..(13)
<223> OTHER INFORMATION: C or L
<220> FEATURE:
<221> NAME/KEY: MISC_FEATURE
<222> LOCATION: (15)..(15)
<223> OTHER INFORMATION: V or I
<220> FEATURE:
<221> NAME/KEY: MISC_FEATURE
<222> LOCATION: (19)..(19)
<223> OTHER INFORMATION: F or I
<220> FEATURE:
<221> NAME/KEY: MISC_FEATURE
<222> LOCATION: (23)..(23)
<223> OTHER INFORMATION: I or V
```

```
<400> SEQUENCE: 188

Gly Xaa Xaa Asn Xaa Val Ser Xaa Xaa His Xaa Gly Xaa Leu Xaa His
1               5                   10                  15

Gly Cys Xaa Asn Ala Ser Xaa Pro Lys
            20              25
```